(12) United States Patent
Schilling et al.

(10) Patent No.: US 11,628,065 B2
(45) Date of Patent: Apr. 18, 2023

(54) MICROCHANNELS IN SUBCHONDRAL BONE AND MEMBRANES COMPRISING SAME FOR THE TREATMENT OF OSTEOARTHRITIS

(71) Applicant: Georg-August-Universitaet Goettingen Stiftung Oeffentlichen Rechts Universitaetsmedizin, Goettingen (DE)

(72) Inventors: Arndt F. Schilling, Goettingen (DE); Shahed Taheri, Goettingen (DE)

(73) Assignee: Georg-August-Universität Göttingen Stiftung Öffentlichen Rechts, Universitätsmedizin, Goettingen (DE)

(*) Notice: Subject to any disclaimer, the term of this patent is extended or adjusted under 35 U.S.C. 154(b) by 40 days.

(21) Appl. No.: 16/828,444

(22) Filed: Mar. 24, 2020

(65) Prior Publication Data

US 2021/0298907 A1    Sep. 30, 2021

(51) Int. Cl.
*A61F 2/00*        (2006.01)
*A61F 2/30*        (2006.01)
(Continued)

(52) U.S. Cl.
CPC ........ *A61F 2/30771* (2013.01); *A61F 2/0063* (2013.01); *A61F 2/32* (2013.01); *A61F 2/38* (2013.01); *A61F 2/3804* (2013.01); *A61F 2/40* (2013.01); *A61F 2002/0081* (2013.01); *A61F 2002/30011* (2013.01);
(Continued)

(58) Field of Classification Search
CPC ................ A61F 2/30771; A61F 2/0063; A61F 2002/0081; A61F 2002/30784; A61F 2002/30838; A61F 2/30756; A61F 2002/30751; A61F 2002/30757; A61F 2002/30761; A61F 2002/0068; A61F 2002/30772; A61F 2/32; A61F 2/38; A61F 2/3804; A61F 2002/30766; A61F 2/30767; A61F 2002/30003; A61F 2/3603; A61L 27/40; A61L 27/44; A61L 2430/24
See application file for complete search history.

(56) References Cited

U.S. PATENT DOCUMENTS

| | | | | |
|---|---|---|---|---|
| 2011/0262696 | A1* | 10/2011 | Bayon | A61F 2/0045 428/131 |
| 2018/0055643 | A1* | 3/2018 | Castro | A61L 27/58 |
| 2018/0361025 | A1* | 12/2018 | Lancaster | A61L 27/56 |

OTHER PUBLICATIONS

Svensson et al ("Bacterial cellulose as a potential scaffold for tissue engineering of cartilage", Biomaterials 26 (2005) 419-431). (Year: 2005).*

(Continued)

*Primary Examiner* — Keri J Nelson
*Assistant Examiner* — Rebecca Lynee Zimmerman
(74) *Attorney, Agent, or Firm* — Stacey J. Farmer

(57) ABSTRACT

The present invention relates to the diagnosis and treatment of joint-related diseases, in particular osteoarthritis. Based on the analysis of the microarchitecture, such as microchannels, of the subchondral bone, the present invention provides methods for evaluating the health state of a joint as well as determining whether a joint is prone to develop or has already developed a disease correlated to joint and cartilage destruction. The invention further provides for membranes and other implants mimicking healthy subchondral bone structure suitable for promoting regeneration of joint structure and function.

11 Claims, 8 Drawing Sheets

(51) Int. Cl.
  *A61F 2/32*  (2006.01)
  *A61F 2/38*  (2006.01)
  *A61F 2/40*  (2006.01)

(52) U.S. Cl.
  CPC .............. *A61F 2002/30777* (2013.01); *A61F 2002/30784* (2013.01); *A61F 2002/30838* (2013.01)

(56) References Cited

OTHER PUBLICATIONS

Taheri et al., "Developmental Transformation and Reduction of Connective Cavities within the Subchondral Bone" Int. J. Mol. Sci., 2019;20(3):770.

Tegner et al., "Rating systems in the evaluation of knee ligament injuries" Clin. Orthop. Relat. Res., 1985;198:43-49.

Woods et al., "Subchondral vascularity in the human femoral head" Ann. Rheum. Dis., 1970;29:138-142.

Yuan et al., "Bone—cartilage interface crosstalk in osteoarthritis: potential pathways and future therapeutic strategies" Osteoarthr. Cartil., 2014;22:1077-1089.

Chen et al., "Osteoarthritis: toward a comprehensive understanding of pathological mechanism" Bone Res., 2017;5:16044.

Chen et al., "Drilling and Microfracture Lead to Different Bone Structure and Necrosis during . . . " Journal of Orthopaedic Research, 2009;27(11):1432-1438.

Goldring et al., "Alterations in periarticular bone and cross talk between subchondral bone and articular cartilage in . . . " Ther. Adv. Musculoskelet. Dis., 2012;4:249-258.

Holzer, "Die Bedeutung des subchondralen Knochens bei der Initiation und Progression der . . . " Journal für Mineralstoffwechsel & Muskoskelettale Erkrankungen, 2017;24(1):4-8.

Irrgang et al., "Development and Validation of the International Knee Documentation Committee Subjective Knee Form" Am. J. Sports Med., 2001;29:600-613.

Loeser et al., "Osteoarthritis: a disease of the joint as an organ" Arthritis Rheum., 2012;64:1697-707.

Lyons et al., "The normal human chondro-osseous junctional region: evidence for contact of uncalcified cartilage . . . " BMC Musculoskelet. Disord., 2006;7(52).

Lysholm et al., "Evaluation of knee ligament surgery results with special emphasis on use of a scoring scale" Am. J. Sports Med., 1982;10:150-154.

Orth et al., "Effect of Subchondral Drilling on the Microarchitecture of Subchondral Bone: Analysis in a Large Animal Model at . . . " Am. J. Sports Med., 2012;40(4):828-836.

Steadman et al., "Microfracture to treat full-thickness chondral defects: surgical technique, rehabilitation, and outcomes" J. Knee Surg., 2002;15:170-176.

* cited by examiner

FIG. 1A
FIG. 1B
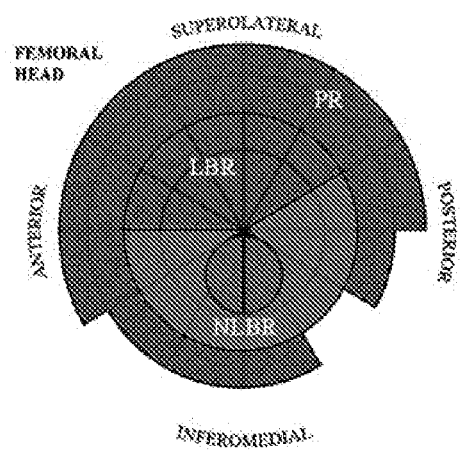
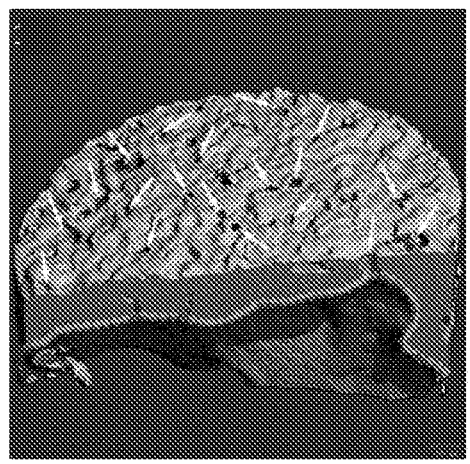
FIG. 1C
FIG. 1D
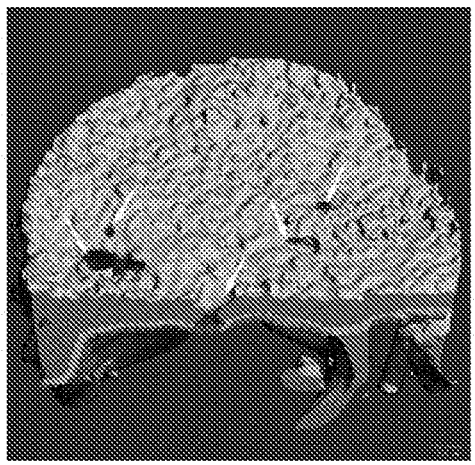
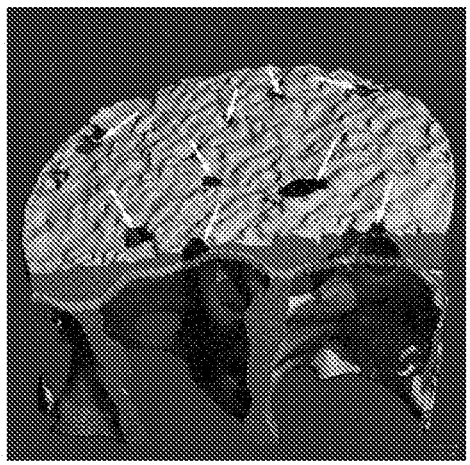

MICROCHANNELS IN SUBCHONDRAL BONE AND MEMBRANES COMPRISING SAME FOR THE TREATMENT OF OSTEOARTHRITIS

FIELD OF THE INVENTION

The present invention relates to diagnosing and treating joint-related diseases, which are accompanied by cartilage destruction and loss. The analysis of subchondral bone microarchitecture and structure allows for the evaluation of the health state of the bony structures within the analyzed joint and the diagnosis of joint-destructive diseases such as osteoarthritis. Modification of the microarchitecture of the subchondral bone may lead to stabilization or even amelioration of the health state of the joint, accompanied by cartilage regeneration. The invention further provides for a membrane and an implant that mimic the healthy subchondral bone microarchitecture thereby allowing for the regeneration of the bony and cartilaginous structures of the joint as well as its functionality.

BACKGROUND OF THE INVENTION

Articular cartilage (AC) and subchondral bone (SB) interact cooperatively and synergistically through a complex interface, which influences the functionality and the degree of health of an entire joint [1, 2]. In this respect, it is now widely accepted that joint diseases such as osteoarthritis (OA) are diseases impacting the whole joint, affecting not only the AC, but also the microstructure of the SB [3, 4].

The SB has previously been found to comprise "breaks" or "defects", herein also called "microchannels" [5, 6]. These microchannels have been proposed to play a role in the nutrient transport to the overlying cartilage, as well as the waste disposal from the joint and synovial efflux. Thus, cartilage nutrition and drainage appear to be highly dependent on the presence and functionality of microchannel structures within the SB, i.e. the microarchitecture of the subchondral bone seems to have a huge impact on cartilage vitality and longevity.

However, in diseased conditions like osteoarthritis, this interplay between SB and cartilage appears to be impaired, ultimately leading to cartilage destruction and catastrophic changes in the SB microarchitecture. While it is still a matter of debate which one comes first, it is a fact that these two developments are hallmarks of joint destruction and disease progression [7].

Based on the above findings, the present inventors developed a method for determining the health state of a joint and its disposition for developing a joint-destructive disease, like osteoarthritis, by analyzing subchondral bone microarchitecture. The invention further provides a biocompatible membrane and/or an implant allowing for the replacement and finally regeneration of the damaged subchondral bone and cartilage structures.

SUMMARY OF THE INVENTION

The present invention relates to a biocompatible membrane comprising a plurality of through holes, i.e. microchannels, wherein the membrane comprises 20 or less through holes per $mm^2$ of membrane.

In one embodiment, the membrane comprises 10 or less through holes per $mm^2$ of membrane. In another embodiment, the membrane comprises between 5 and 15 through holes per $mm^2$ of membrane. In a preferred embodiment, the membrane comprises 10 through holes per $mm^2$ of membrane. In some embodiments, each of the plurality of through holes defines a cross-sectional area of between 800 and 4000 $\mu m^2$. In preferred embodiments, each of the plurality of through holes defines a cross-sectional area of between 1200 and 2500 $\mu m^2$. In even more preferred embodiments, each of the plurality of through holes defines a cross-sectional area of between 1600 and 1800 $\mu m^2$.

In alternative embodiments, the through holes of the membrane are arranged in a size and distribution pattern that correspond to the pattern of microchannels of one or more of the load bearing region, non-load bearing region or peripheral rim of subchondral bone, so that the membrane comprising a plurality of through holes is divided in one or more of a load bearing region section, a non-load bearing region section and/or a peripheral rim section.

In preferred embodiments, each of the through holes in the load bearing region section defines a cross-sectional area of between 800 and 1600 $\mu m^2$, each of the through holes in the non-load bearing region section defines a cross-sectional area of between 1600 and 2500 $\mu m^2$, and each of the through holes in the peripheral rim section defines a cross-sectional area of between 2500 and 4000 $\mu m^2$.

In even more preferred embodiments, the load bearing region section comprises 10 through holes per $mm^2$ membrane and each of the through holes defines a cross-sectional area of 1200 $\mu m^2$, the non-load bearing region section comprises 4 through holes per $mm^2$ membrane and each of the through holes defines a cross-sectional area of 1800 $\mu m^2$, and the peripheral rim section comprises 6 through holes per $mm^2$ membrane and each of the through holes defines a cross-sectional area of 3500 $\mu m^2$.

In some embodiments, the thickness of the membrane is 50-150 $\mu m$. In some embodiments, the thickness of the membrane is 50-100 $\mu m$. In some embodiments, the thickness of the membrane is 100-150 $\mu m$. In a preferred embodiment of the invention, the thickness of the membrane is 150 $\mu m$. In some embodiments, at least one or more of the through holes are confined to an angle of between 65-89 degrees relative to the surface of the membrane.

In some embodiments, the cross-sectional area of at least some of the through holes increases or decreases by up to 50% throughout the membrane, compared to the cross-sectional area of the respective hole at the surface of the membrane.

In some embodiments, the permeability of the membrane corresponds to the permeability of a patient's healthy joint.

In some preferred embodiments, the membrane comprises polycaprolactone. In some even more preferred embodiments, the membrane consists of polycaprolactone.

In some embodiments, the membrane comprises more than one layer.

In some embodiments, the biocompatible membrane comprises more than two layers.

In some embodiments, the biocompatible membrane further comprises cells adhered thereto.

In preferred embodiments, the biocompatible membrane is biodegradable.

The invention further provides for an implant comprising a plurality of through holes.

In some embodiments, the implant comprises 20 or less through holes per $mm^2$ of implant. In another embodiment, the implant comprises 10 or less through holes per $mm^2$ of implant. In still another embodiment, the implant comprises between 5 and 15 through holes per $mm^2$ of implant. In a preferred embodiment, the implant comprises 10 through holes per $mm^2$ of implant.

In some embodiments, each of the plurality of through holes of the implant defines a cross-sectional area of between 800 and 4000 μm². In some preferred embodiments, each of the plurality of through holes of the implant defines a cross-sectional area of between 1200 and 2500 μm². In some even more preferred embodiments, each of the plurality of through holes of the implant defines a cross-sectional area of between 1600 and 1800 μm².

In alternative embodiments, the through holes of the implant are arranged in a size and distribution pattern that corresponds to the pattern of microchannels of one or more of the load bearing region, non-load bearing region or peripheral rim of subchondral bone, so that the implant comprising a plurality of through holes is divided in one or more of a load bearing region section, a non-load bearing region section and/or a peripheral rim section.

In preferred embodiments, each of the through holes in the load bearing region section defines a cross-sectional area of between 800 and 1600 μm², each of the through holes in the non-load bearing region section defines a cross-sectional area of between 1600 and 2500 μm², and each of the through holes in the peripheral rim section defines a cross-sectional area of between 2500 and 4000 μm².

In even more preferred embodiments, the load bearing region section comprises 10 through holes per mm² implant and each of the through holes defines a cross-sectional area of 1200 μm², the non-load bearing region section comprises 4 through holes per mm² implant and each of the through holes defines a cross-sectional area of 1800 μm², and the peripheral rim section comprises 6 through holes per mm² implant and each of the plurality of through holes defines a cross-sectional area of 3500 μm².

In some embodiments, at least some of the through holes of the implant confine an angle of between 65-89 degrees with the surface of the implant.

In some embodiments, the cross-sectional area of at least some of the through holes of the implant increases or decreases by up to 50% throughout the membrane, compared to the cross-sectional area of the respective hole at the surface of the membrane.

In some embodiments, the implant comprises more than one layer.

In some embodiments, the implant comprises more than two layers.

In some embodiments, the implant further comprises cells adhered thereto.

Preferably, the implant is a joint implant. In some embodiments, the implant is a hip, knee, elbow, or shoulder implant. Most preferably, the implant is a knee implant.

In some embodiments, the implant comprises one or more of a metal, ceramic, polymer, preferably polycaprolactones, biological materials, hydroxyapatite, cells, or combinations thereof.

The invention further provides for a method of diagnosing the health state of a joint of a subject, wherein the method comprises a step a) determining the number of microchannels present in the subchondral tissue of a subject; a step b) determining the average size of the microchannels of the SB tissue; a step c) comparing data obtained in steps a) and b) with reference data; and a step d) determining on the basis of c) the health state of the joint; wherein a number of microchannels between 0 and 6 per mm² or 15 per mm² and more than 15 per mm² in the load bearing region of the joint and/or an average size of the cross-sectional area of microchannels between 0 and 800 μm² or 14,000 and above 14,000 μm² indicate joint damage.

In some embodiments, the method is for monitoring destruction of a joint of a subject, and wherein step c) comprises comparing data obtained in step b) with reference data obtained from the same joint at an earlier time point.

In some embodiments, the method is for diagnosing atherosclerosis in a subject.

In some embodiments, the joint is a knee joint.

In some embodiments, the subject is a mammal.

In preferred embodiments, the subject is human.

The invention further provides for a first method of treating a joint of a subject in need thereof, wherein the method comprises a step a) introducing through holes into the subchondral bone; and optionally a step b) applying a membrane of the invention to the subchondral bone. In some embodiments, the membrane is fixed by fibrinogen glue to the bony tissue.

In some preferred embodiments, the joint is a knee joint.

In preferred embodiments, the subject is a mammal.

In even more preferred embodiments, the subject is human.

In some embodiments of the method for treating a joint of a subject, the through holes are arranged in a pattern of 20 or less through holes per mm² on the subchondral bone. In some embodiments of the method for treating a joint of a subject, the through holes are arranged in a pattern of 10 or less through holes per mm² on the subchondral bone. In some embodiments of the method for treating a joint of a subject, the through holes are arranged in a pattern of between 5 and 15 through holes per mm² on the subchondral bone. In some embodiments of the method for treating a joint of a subject, the through holes are arranged in a pattern of 10 through holes per mm² on the subchondral bone.

In alternative embodiments, the through holes introduced in the subchondral bone in step a) are arranged in a size and distribution pattern that correspond to the pattern of microchannels of one or more of the load bearing region, non-load bearing region or peripheral rim of healthy subchondral bone.

In preferred embodiments, each of the through holes introduced in the load bearing region defines a cross-sectional area of between 800 and 1600 μm², each of the through holes introduced in the non-load bearing region defines a cross-sectional area of between 1600 and 2500 μm², and each of the through holes introduced in the peripheral rim defines a cross-sectional area of between 2500 and 4000 μm².

In even more preferred embodiments, the load bearing region after step a) comprises 10 through holes per mm² of subchondral bone and each of the through holes defines a cross-sectional area of 1200 μm², the non-load bearing region comprises 4 through holes per mm² of subchondral bone and each of the through defines a cross-sectional area of between 1800 μm², and the peripheral rim comprises 6 through holes per mm² of subchondral bone and each of the through holes defines a cross-sectional area of 3500 μm².

In some embodiments of the method for treating a joint of a subject, the through holes comprise a length of at least 200 μm measured from the surface of the subchondral bone.

In some embodiments of the method for treating a joint of a subject, the through holes comprise a length corresponding to the thickness of the subchondral bone of the subject.

In some embodiments of the method for treating a joint of a subject, the through holes form a continuous opening from the upper surface of the subchondral bone of the subject to the underlying trabecular spacings, which contain bone marrow and vascular structures.

The invention further provides for a second method of treating a joint of a subject in need thereof, wherein the method comprises a step a) removing diseased subchondral bone tissue from the joint; and a step b) inserting a membrane comprising through holes into the subject thereby replacing the diseased subchondral bone tissue removed in step a).

The invention further provides for an alternative of the second method of treating a joint of a subject in need thereof, wherein the method comprises a step a) removing diseased subchondral bone tissue from the joint of the subject; and a step b) inserting an implant comprising through holes into the subject thereby replacing the diseased subchondral bone tissue removed in step a).

In some embodiments, the joint is a knee joint.

In preferred embodiments, the subject is a mammal.

In even more preferred embodiments, the subject is human.

BRIEF DESCRIPTION OF THE DRAWINGS

FIG. 1A to FIG. 1D depict the microstructure of samples of human hip joint bone with specific focus on microchannel morphology. The surface of human hip joints was divided into zones based on the loading history and analyzed by micro-CT imaging (LBR: load bearing region; NLBR: non-load bearing region; PR: peripheral rim).

FIG. 5 collectively shows a scheme for implantation of preferred embodiments of membranes in different areas (peripheral rim (PR, 1), load bearing region (LBR, 2), non-load bearing region (NLBR, 3)) of a knee joint.

DETAILED DESCRIPTION OF THE INVENTION

Definitions

Figure 2A:
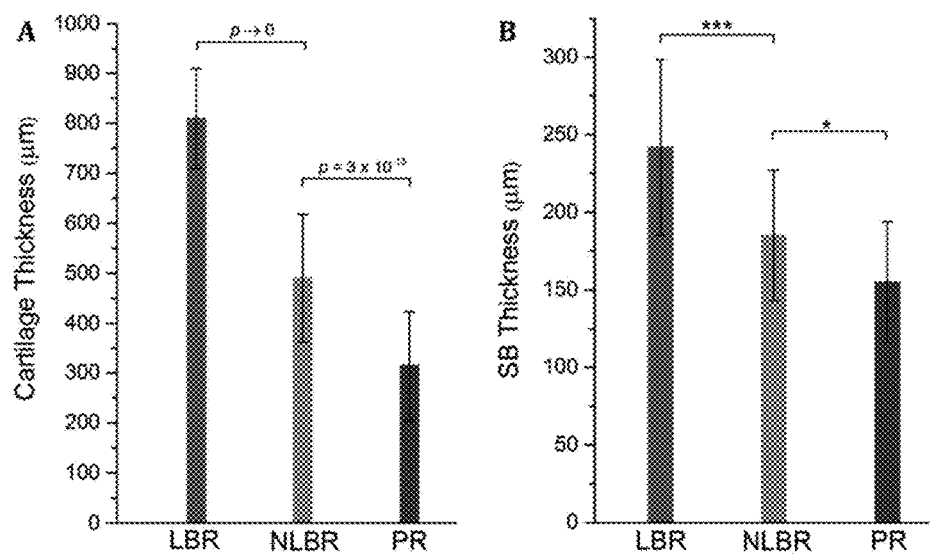
FIG. 2A-FIG. 2E collectively show graphs presenting patterns of cartilage thickness, microchannel distribution, microchannel number, and sizes in the different zones as analyzed before. LBR, NLBR, and PR stand for the "load bearing region", "non-load bearing region", and the "peripheral rim", respectively. Feret is the maximum caliper diameter of a hole, and is defined as the longest distance between any two points along the selection boundary. The minimum caliper diameter (MinFeret) was measured to calculate the shortest distance inside of the channels.

Biocompatible: The term biocompatible herein refers to the ability of a material to be in contact with a living system without producing an adverse effect. It may also refer to the ability of a material to be in contact with a living system with only an appropriate, tolerable host response for a specific application. Non-limiting examples include metals, including titanium, polymers, such as polyvinyl chloride (PVC), polyethylene (PE), polypropylene (PP), polymethylmetacrylate (PMMA), polyethylene terephthalate (PET), compositions, such as bone cement, or ceramics, including $Al_2O_3$, $ZrO_2$, and hydroxyapatite.

Biodegradable: The terms biodegradable and absorbable are synonymously used herein. A material that is biodegradable is understood to a material capable of being broken down and completely absorbed by cells under physiological conditions present within a body of a subject; after a period of time, the material is no longer detectable in the subject's body.

Cross-sectional area: Cross-sectional area as used herein is the area of a two-dimensional shape that is obtained when a three-dimensional object, such as a microchannel or through hole, is intersected with a plane parallel to its base.

Diseased: The term diseased as used herein relates to the state of a tissue or joint, wherein the tissue or joint is damaged due to the development, onset or progression of joint-destructive diseases. Damaged is to be understood as a structural change of the tissue or joint that is accompanied by negative consequences as to the functionality of the tissue or joint or by pain.

Implant: An implant is a medical device manufactured to be introduced into a body of a subject to replace a missing biological structure, support a damaged biological structure, or enhance an existing biological structure. Exemplary implants comprise implants that correspond to the shape of the biological structure they replace, artificial joint implants and membranes.

Healthy: The term healthy as used herein relates to the state of a joint, cartilage, subchondral bone or any other tissue that is not damaged, i.e. the microarchitecture or structure of the respective tissue has not undergone a change accompanied by negative consequences as to the functionality of the tissue or joint.

Membrane: The term membrane as used herein refers to a thin soft pliable sheet or layer.

Microchannel: The term microchannel is used herein interchangeably with through hole. Microchannels or through holes provide for a continuous opening within the membrane or implant connecting the base (bone facing) surface with the upper (synovium facing) surface. With respect to through holes or microchannels introduced into subchondral bone of a subject, through holes or microchannels are considered to be a continuous opening from the upper (synovium facing) surface of the subchondral bone to the base of the diseased subchondral bone region that has to be treated by introducing such through holes.

Significant: A difference between two values is herein considered significant if the values deviate from one other with a confidence interval of 0.05.

Thickness: The thickness of a membrane as used herein is intended to define the extension of the membrane from its base (bone facing) surface to its upper (synovium facing surface).

Through holes: As described above, through holes and microchannels are used interchangeably herein.

Advantages Provided by the Present Invention

One advantage identified by the present inventors is the finding that the microarchitecture of the subchondral bone correlates with cartilage appearance and health state. In many joint-related diseases, such as osteoarthritis, cartilage destruction is a hallmark of the onset and development of these diseases and is accompanied by changes in subchondral bone microarchitecture, particularly with respect to number and size of microchannels. The inventors found that the microarchitecture of the subchondral bone differs between distinct regions of the subchondral bone, i.e. load bearing region, non-load bearing region and peripheral rim, and that these differences may also lead to different structural changes upon onset of joint-destructive diseases.

Based on these findings, it was recognized that by modifying the microarchitecture of the subchondral bone, damaged or destroyed cartilage tissue may be regenerated and joint destruction attenuated. The inventors also observed that the more closely a modified subchondral bone microarchitecture in a diseased joint mimics the microarchitecture of SB in a healthy joint, the better the outcome of disease progression and cartilage regeneration. Hence, the invention provides for several aspects of modifying subchondral bone microarchitecture by re-establishing a healthy number of healthy sized microchannels in subchondral bone in order to restore healthy or close-to-healthy conditions in the joint, in particular with respect to cartilage regeneration. The invention provides also for aspects of modifying SB microarchitecture such that the size, number and distribution of microchannels varies dependent on, and is adapted to, LBR, NLBR and PR region of the SB thereby allowing for a particularly accurate imitation of healthy SB microarchitecture.

However, as the interplay between subchondral bone and articular cartilage is complex; there is only a fine line between too few and too many microchannels, or too small and too large microchannels, within the subchondral bone or respective replacement materials, such as implants.

Thus, the present invention provides for membranes, implants and methods of applying such membranes and implants for treating the joint of a subject, which comprises an advantageous number and advantageous dimensions of these microchannels, thereby maintaining the crucial balance between permeability and stability of the subchondral bone. Advantageous membranes and implants according to the invention may also comprise microchannels having a size and distribution that is adapted to LBR, NLBR and PR region of healthy subchondral bone microarchitecture. The restoration of such healthy microchannel architecture improves in turn the overall status of the diseased joint. The restoration of the microchannel architecture can also lead to restoration of cartilage.

In addition, in especially preferred embodiments, the membrane of the invention is biodegradable, allowing for the complete resorption of the membrane by invading cells and the re-establishment of a "healthy" or "close-to-healthy" state of the joint without any artificial supports remaining therein.

EMBODIMENTS

Membrane

Figure 4:
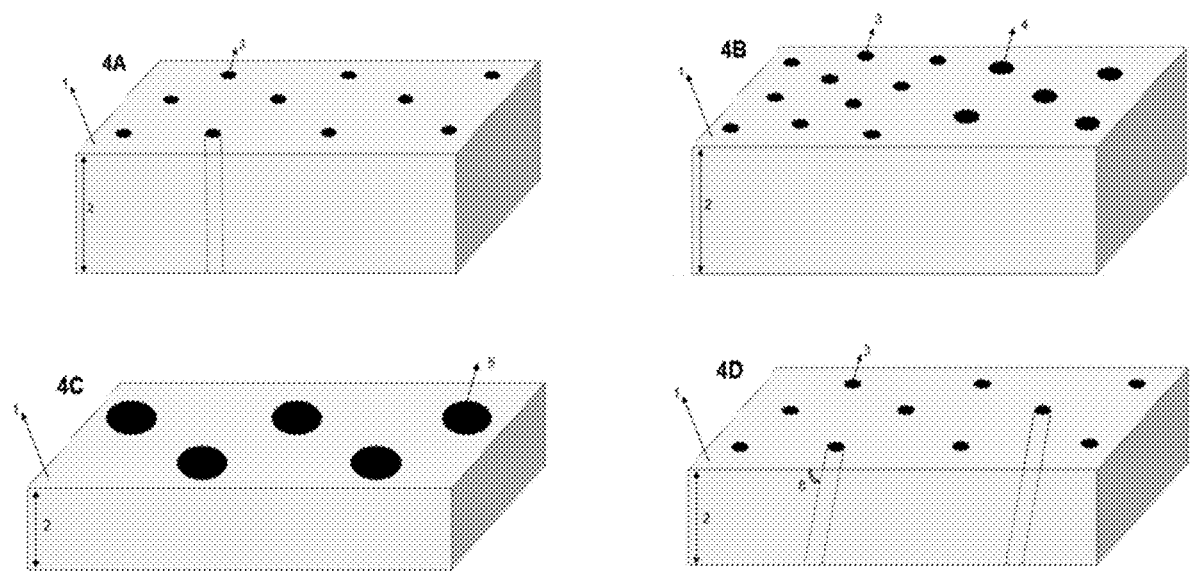
FIG. 4 is a schematic illustrating different configurations of the membrane comprising through holes according to various embodiments of the invention, wherein 1: membrane, 2: membrane's thickness, 3: through hole of 800 µm² cross sectional area, 4: through hole of 1200 µm² cross sectional area, 5: through hole of 3500 µm² cross sectional area and 6: angle confined by through holes with upper surface of membrane.

A membrane of the present invention comprises through holes, also called microchannels. The membrane is biocompatible. The through holes are arranged in a pattern of 20 or less through holes per $mm^2$ membrane. In some preferred embodiments, the membrane comprises polycaprolactone. Exemplary membrane embodiments are illustrated in FIG. 4.

The through holes of the membrane provide for a continuous opening through the membrane connecting the base (bone facing) surface with the upper (synovium facing) surface.

The through holes may be arranged perpendicularly (90 degrees) to the surface of the membrane. In other embodiments, the through holes are arranged at an angle to the surface of the membrane, which is beneficial to mimic the microstructure of the healthy SB. The through holes may then confine an angle of between 1-89 degrees with the surface of the membrane. In some embodiments, the through holes confine an angle of between 20-89 degrees with the surface of the membrane. In some embodiments, the through holes confine an angle of between 45-89 degrees with the surface of the membrane. In some embodiments, the through holes confine an angle of between 45-70 degrees with the surface of the membrane. In preferred embodiments, the through holes confine an angle of between 65-89 degrees with the surface of the membrane. Exemplary angles are 65, 70, 75, 80, 85, 89 degrees.

The through holes of the membrane may further be arranged identically to one another in their opening-to-opening direction. In some embodiments, the through holes of the membrane are arranged differently to one another in their opening-to-opening direction. In some embodiments, some of the through holes are perpendicular to the surface of the membrane and others may confine an angle of between 1-89 degrees with the surface of the membrane.

The through holes may be arranged in a specific pattern within the membrane. In some embodiments, the through holes are arranged on the membrane such that the distances between them are identical. In some embodiments, the plurality of through holes is arranged along a gradient with only a few though holes at one portion of the membrane and significantly more through holes in one or more other portion of the membrane. In other embodiments, the through holes are arranged not in a specific pattern within the membrane, but are dispersed randomly within the membrane.

The number of through holes within the membrane may be specifically defined. In some embodiments, the membrane comprises no more than 5, 6, 7, 8, 9, 10, 11, 12, 13, 14, 15, 16, 17, 18, 19, or 20 through holes per $mm^2$ of membrane. In some embodiments, the membrane comprises 20 or less through holes per $mm^2$ of membrane. In another embodiment, the membrane comprises 10 or less through holes per $mm^2$ of membrane. In another embodiment, the membrane comprises between 5 and 15 through holes per $mm^2$ of membrane. In preferred embodiments, the membrane comprises 10 through holes per $mm^2$ of membrane.

Furthermore, in some embodiments, each through hole defines a cross-sectional area of between 800 and 4000 $\mu m^2$. In preferred embodiments, each through hole defines a cross-sectional area of between 1200 and 2500 $\mu m^2$. In more preferred embodiments, each through hole defines a cross-sectional area of between 1600 and 1800 $\mu m^2$. In even more preferred embodiments, each through hole defines a cross-sectional area of 1800 $\mu m^2$.

In one exemplary embodiment, each through hole defines a cross-sectional area of around 1000 µm². In one exemplary embodiment, each through hole defines a cross-sectional area of around 1500 µm². In one exemplary embodiment, each through hole defines a cross-sectional area of around 1600 µm². In one exemplary embodiment, each through hole defines a cross-sectional area of around 1700 µm². In one exemplary embodiment, each through hole defines a cross-sectional area of around 1800 µm². In one exemplary embodiment, each through hole defines a cross-sectional area of around 1900 µm². In one exemplary embodiment, each through hole defines a cross-sectional area of around 2000 µm². In one exemplary embodiment, each through hole defines a cross-sectional area of around 2500 µm². In one exemplary embodiment, each through hole defines a cross-sectional area of around 3000 µm². In one exemplary embodiment, each through hole defines a cross-sectional area of around 3500 µm². In one exemplary embodiment, each through hole defines a cross-sectional area of around 4000 µm².

In some embodiments, the membrane comprises less than 20 through holes per mm² of membrane, each with a cross-sectional area of between 1200 and 2500 µm². In some embodiments, the membrane comprises less than 20 through holes per mm² of membrane, each with a cross-sectional area of between 1200 and 2500 µm², wherein at least some of the through holes confine an angle with the upper surface of the membrane of between 65-89 degrees. In another embodiment, the membrane comprises less than 20 through holes per mm² of membrane, each with a cross-sectional area of 2500 µm². In some embodiments, the membrane comprises less than 20 through holes per mm² of membrane, each with a cross-sectional area of 2500 µm², wherein at least some of the through holes confine an angle with the upper surface of the membrane of between 65-89 degrees. In another embodiment, the membrane comprises less than 20 through holes per mm² of membrane, each with a cross-sectional area of 1800 µm². In some embodiments, the membrane comprises less than 20 through holes per mm² of membrane, each with a cross-sectional area of 1800 µm², wherein at least some of the through holes confine an angle with the upper surface of the membrane of between 65-89 degrees. In another embodiment, the membrane comprises less than 20 through holes per mm² of membrane, each with a cross-sectional area of 1200 µm². In some embodiments, the membrane comprises less than 20 through holes per mm² of membrane, each with a cross-sectional area of 1200 µm², wherein at least some of the through holes confine an angle with the upper surface of the membrane of between 65-89 degrees.

In some embodiments, the membrane comprises less than 10 through holes per mm² of membrane, each with a cross-sectional area of between 1200 and 2500 µm². In some embodiments, the membrane comprises less than 10 through holes per mm² of membrane, each with a cross-sectional area of between 1200 and 2500 µm², wherein at least some of the through holes confine an angle with the upper surface of the membrane of between 65-89 degrees. In another embodiment, the membrane comprises less than 10 through holes per mm² of membrane, each with a cross-sectional area of 2500 µm². In some embodiments, the membrane comprises less than 10 through holes per mm² of membrane, each with a cross-sectional area of 2500 µm², wherein at least some of the through holes confine an angle with the upper surface of the membrane of between 65-89 degrees. In another embodiment, the membrane comprises less than 10 through holes per mm² of membrane, each with a cross-sectional area of 1800 µm². In some embodiments, the membrane comprises less than 10 through holes per mm² of membrane, each with a cross-sectional area of 1800 µm², wherein at least some of the through holes confine an angle with the upper surface of the membrane of between 65-89 degrees. In another embodiment, the membrane comprises less than 10 through holes per mm² of membrane, each with a cross-sectional area of 1200 µm². In some embodiments, the membrane comprises less than 10 through holes per mm² of membrane, each with a cross-sectional area of 1200 µm², wherein at least some of the through holes confine an angle with the upper surface of the membrane of between 65-89 degrees.

In some embodiments, the membrane comprises between 10 and 20 through holes per mm² of membrane, each with a cross-sectional area of between 1200 and 2500 µm². In some embodiments, the membrane comprises between 10 and 20 through holes per mm² of membrane, each with a cross-sectional area of between 1200 and 2500 µm², wherein at least some of the through holes confine an angle with the upper surface of the membrane of between 65-89 degrees. In another embodiment, the membrane comprises between 10 and 20 through holes per mm² of membrane, each with a cross-sectional area of 2500 µm². In some embodiments, the membrane comprises between 10 and 20 through holes per mm² of membrane, each with a cross-sectional area of 2500 µm², wherein at least some of the through holes confine an angle with the upper surface of the membrane of between 65-89 degrees. In another embodiment, the membrane comprises between 10 and 20 through holes per mm² of membrane, each with a cross-sectional area of 1800 µm². In some embodiments, the membrane comprises between 10 and 20 through holes per mm² of membrane, each with a cross-sectional area of 1800 µm², wherein at least some of the through holes confine an angle with the upper surface of the membrane of between 65-89 degrees. In another embodiment, the membrane comprises between 10 and 20 through holes per mm² of membrane, each with a cross-sectional area of 1200 µm². In some embodiments, the membrane comprises between 10 and 20 through holes per mm² of membrane, each with a cross-sectional area of 1200 µm², wherein at least some of the through holes confine an angle with the upper surface of the membrane of between 65-89 degrees.

In another embodiment, the membrane comprises between 5 and 15 through holes per mm² of membrane, each with a cross-sectional area of between 1200 and 2500 µm². In some embodiments, the membrane comprises between 5 and 15 through holes per mm² of membrane, each with a cross-sectional area of between 1200 and 2500 µm², wherein at least some of the through holes confine an angle with the upper surface of the membrane of between 65-89 degrees. In another embodiment, the membrane comprises between 5 and 15 through holes per mm² of membrane, each with a cross-sectional area of 2500 µm². In some embodiments, the membrane comprises between 5 and 15 through holes per mm² of membrane, each with a cross-sectional area of 2500 µm², wherein at least some of the through holes confine an angle with the upper surface of the membrane of between 65-89 degrees. In another embodiment, the membrane comprises between 5 and 15 through holes per mm² of membrane, each with a cross-sectional area of 1800 µm². In some embodiments, the membrane comprises between 5 and 15 through holes per mm² of membrane, each with a cross-sectional area of 1800 µm², wherein at least some of the through holes confine an angle with the upper surface of the membrane of between 65-89 degrees. In another embodiment, the membrane comprises between 5 and 15 through holes per $mm^2$ of membrane, each with a cross-sectional area of 1200 $\mu m^2$. In some embodiments, the membrane comprises between 5 and 15 through holes per $mm^2$ of membrane, each with a cross-sectional area of 1200 $\mu m^2$, wherein at least some of the through holes confine an angle with the upper surface of the membrane of between 65-89 degrees.

In a preferred embodiment, the membrane comprises 10 through holes per $mm^2$ of membrane, each with a cross-sectional area of between 1200 and 2500 $\mu m^2$. In preferred embodiments, the membrane comprises 10 through holes per $mm^2$ of membrane, each with a cross-sectional area of between 1200 and 2500 $\mu m^2$, wherein at least some of the through holes confine an angle with the upper surface of the membrane of between 65-89 degrees. In an even more preferred embodiment, the membrane comprises 10 through holes per $mm^2$ of membrane, each with a cross-sectional area of 1800 $\mu m^2$. In another even more preferred embodiments, the membrane comprises 10 through holes per $mm^2$ of membrane, each with a cross-sectional area of 1800 $\mu m^2$, wherein at least some of the through holes confine an angle with the upper surface of the membrane of between 65-89 degrees.

In another embodiment, the membrane comprises 10 through holes per $mm^2$ of membrane, each with a cross-sectional area of 1200 $\mu m^2$. In another embodiment, the membrane comprises 10 through holes per $mm^2$ of membrane, each with a cross-sectional area of 1200 $\mu m^2$, wherein at least some of the through holes confine an angle with the upper surface of the membrane of between 65-89 degrees.

The through holes may further be arranged on the membrane in a pattern of size and distribution (number of through holes per $mm^2$ membrane) to substantially match the healthy subchondral bone microarchitecture. Thus, corresponding to subchondral bone, the membrane may be divided in distinct sections, i.e. load bearing region section, non-load bearing region section and peripheral rim section (Examples 1, 2, and 5).

The membrane may then comprise a specific number of specifically sized through holes in one or more of these sections. In some embodiments, the membrane comprises through holes in the load bearing region section that each define a cross-sectional area of between 800 and 1600 $\mu m^2$. In some embodiments, the membrane comprises through holes in the load bearing region section that each define a cross-sectional area of 1200 $\mu m^2$. In some embodiments, the membrane comprises through holes in the non-load bearing region section that each define a cross-sectional area of between 1600 and 2500 $\mu m^2$. In some embodiments, the membrane comprises through holes in the non-load bearing region section that each define a cross-sectional area of 1800 $\mu m^2$. In some embodiments, the membrane comprises through holes in the peripheral rim section that each define a cross-sectional area of between 2500 and 4000 $\mu m^2$. In some embodiments, the membrane comprises through holes in the peripheral rim section that each define a cross-sectional area of 3500 $\mu m^2$. In some embodiments, the membrane comprises 5-15 through holes per $mm^2$ membrane in the load bearing region section. In preferred embodiments, the membrane comprises 10 through holes per $mm^2$ membrane in the load bearing region section. In some embodiments, the membrane comprises 2-6 through holes per $mm^2$ membrane in the non-load bearing region section. In preferred embodiments, the membrane comprises 4 through holes per $mm^2$ membrane in the non-load bearing region section. In some embodiments, the membrane comprises 4-8 through holes per $mm^2$ membrane in the peripheral rim section. In preferred embodiments, the membrane comprises 6 through holes per $mm^2$ membrane in the peripheral rim section. In even more preferred embodiments, the membrane comprises 10 through holes per $mm^2$ membrane in the load bearing region section and each of the through holes defines a cross-sectional area of 1200 $\mu m^2$, 4 through holes per $mm^2$ membrane in the non-load bearing region section and each of the through holes defines a cross-sectional area of 1800 $\mu m^2$, and 6 through holes per $mm^2$ membrane in the peripheral rim section and each of the through holes defines a cross-sectional area of 3500 $\mu m^2$.

In some embodiments, the membrane comprises 10 through holes per $mm^2$ membrane in the load bearing region section and each of the through holes defines a cross-sectional area of 1200 $\mu m^2$, 4 through holes per $mm^2$ membrane in the non-load bearing region section and each of the through holes defines a cross-sectional area of 1800 $\mu m^2$, and 6 through holes per $mm^2$ membrane in the peripheral rim section and each of the through holes defines a cross-sectional area of 3500 $\mu m^2$, wherein at least some of the through holes confine an angle with the upper surface of the membrane of between 65-89 degrees.

In some embodiments, the cross-sectional area of the through holes is constant throughout the membrane. In some embodiments, the cross-sectional area of at least some of the through holes increases or decreases by up to 50% throughout the membrane, compared to the cross-sectional area of the respective through hole at a surface of the membrane. In some embodiments, the cross-sectional increases or decreases with a slope of 0.1-0.2 (i.e. 75-300 $\mu m^2$ increase or decrease in cross-sectional area in each 100 $\mu m$ of the membrane's thickness). In other embodiments, the cross-sectional area of the through holes increases or decreases with a slope of 0.5-0.75 (2,000-4,500 $\mu m^2$ increase or decrease in cross-sectional area in each 100 $\mu m$ of the membrane's thickness). In preferred embodiments, the cross-sectional area of the through holes increases or decreases with a slope of 0.2-0.5 (300-2,000 $\mu m^2$ increase or decrease in cross-sectional area in each 100 $\mu m$ of the membrane's thickness).

In further embodiments, the permeability of the membrane comprising a plurality of through holes may be similar to the permeability of a subject's healthy subchondral bone permeability. The permeability of the membrane comprising a plurality of through holes may have at least 50%, at least 60%, at least 70%, at least 80%, at least 90%, at least 95% of the permeability of a subject's healthy subchondral bone. In a preferred embodiment, the permeability of the membrane comprising a plurality of through holes is identical to that of a subject's healthy subchondral bone permeability. In some embodiments, the permeability of the membrane comprising a plurality of through holes may be higher than the permeability of a subject's healthy subchondral bone. The permeability of the membrane comprising a plurality of through holes may have at most 105%, at most 110%, at most 120%, at most 130%, at most 140%, at most 150% of the permeability of a subject's healthy subchondral bone.

The membrane may further be defined by its thickness. Thus, the membrane may be at least 50 $\mu m$ thick. In some embodiments, the thickness of the membrane is less than 150 $\mu m$. In some embodiments, the thickness of the membrane is 50-150 $\mu m$. In some embodiments, the thickness of the membrane is 50-100 $\mu m$. In some embodiments, the thickness of the membrane is 100-150 $\mu m$. In preferred embodiments, the thickness of the membrane is 150 $\mu m$.

In some embodiments, the membrane comprises one or more of polyethylene terephtalate (PET), polyvinyl alcohol (PVA), polybutylene adipate-terephthalate (PBAT), polybutylene succinate (PBS), polycaprolactone (PCL), polyglycolide (PGA), polypropylene (PP), polylactide (PLA), polyether ketone (PEEK). In preferred embodiments, the membrane comprises polycaprolactone. In some embodiments, the membrane consists of one or more of polyethylene terephtalate (PET), polyvinyl alcohol (PVA), polybutylene adipate-terephthalate (PBAT), polybutylene succinate (PBS), polycaprolactone (PCL), polyglycolide (PGA), polypropylene (PP), polylactide (PLA), polyether ketone (PEEK).

In some embodiments, the membrane comprises more than one layer. In some embodiments, the membrane comprises more than two layers. In some embodiments one or more layer of the membrane is selected from the group of consisting of polyethylene terephtalate (PET), polyvinyl alcohol (PVA), polybutylene adipate-terephthalate (PBAT), polybutylene succinate (PBS), polycaprolactone (PCL), polyglycolide (PGA), polypropylene (PP), polylactide (PLA), polyether ketone (PEEK), and collagen. In other embodiments, at least one layer of the membrane comprises hyaluronic acid. In some embodiments, one layer of the membrane comprises porous three-dimensional structures.

Alternatively, the membrane can be manufactured without through holes and the through holes can be introduced by using one or more of a microdrill, a laser ablation system, a water jet, photolithography, soft lithography, film deposition, electron beam lithography, colloid monolayer lithography, etching, microfabrication. In some embodiments, a membrane already containing though holes is manufactured by means of 3D printing, injection molding, rapid prototyping.

In some embodiments, the membrane further comprises cells adhered thereto. Cells adhered to the membrane may be selected from mesenchymal stem cells, chondrocytes, osteoblasts, osteoclasts, osteoprogenitors, bone lining cells, osteocytes, induced pluripotent cells, genetically modified cells. In preferred embodiments, the membrane comprises mesenchymal stem cells adhered thereto.

In even more preferred embodiments, the membrane is biodegradable.

In a preferred embodiment, the biocompatible membrane comprises 10 through holes per $mm^2$ of membrane, each with a cross-sectional area of 1800 $\mu m^2$, is 150 $\mu m$ thick, comprises polycaprolactone and is biodegradable.

In another preferred embodiment, the biocompatible membrane comprises 10 through holes per $mm^2$ of membrane, each with a cross-sectional area of 1800 $\mu m^2$, is 150 $\mu m$ thick, comprises polycaprolactone and is biodegradable, wherein the cross-sectional area of the through holes increases or decreases with a slope of 0.2-0.5 (300-2,000 $\mu m^2$ increase or decrease in cross-sectional area in each 100 $\mu m$ of the membrane's thickness).

In another preferred embodiment, the biocompatible membrane comprises 10 through holes per $mm^2$ of membrane, each with a cross-sectional area of 1800 $\mu m^2$, is 150 $\mu m$ thick, comprises polycaprolactone and is biodegradable, wherein the cross-sectional area of the through holes increases or decreases with a slope of 0.2-0.5 (300-2,000 $\mu m^2$ increase or decrease in cross-sectional area in each 100 $\mu m$ of the membrane's thickness) and at least some of the through holes confine an angle of between 65-89 degrees with the upper surface of the membrane.

In another preferred embodiment, the biocompatible membrane comprises 10 through holes per $mm^2$ of membrane, each with a cross-sectional area of 1800 $\mu m^2$, is 150 $\mu m$ thick, comprises polycaprolactone and is biodegradable, wherein the cross-sectional area of the through holes increases or decreases with a slope of 0.2-0.5 (300-2,000 $\mu m^2$ increase or decrease in cross-sectional area in each 100 $\mu m$ of the membrane's thickness), at least some of the through holes confine an angle of between 65-89 degrees with the upper surface of the membrane, and the membrane comprises mesenchymal stem cells adhered thereto.

In a preferred embodiment, the biocompatible membrane comprises 10 through holes per $mm^2$ of membrane, each with a cross-sectional area of 1800 $\mu m^2$, is 150 $\mu m$ thick, consists of polycaprolactone and is biodegradable.

In another preferred embodiment, the biocompatible membrane comprises 10 through holes per $mm^2$ of membrane, each with a cross-sectional area of 1800 $\mu m^2$, is 150 $\mu m$ thick, consists of polycaprolactone and is biodegradable, wherein the cross-sectional area of the through holes increases or decreases with a slope of 0.2-0.5 (300-2,000 $\mu m^2$ increase or decrease in cross-sectional area in each 100 $\mu m$ of the membrane's thickness).

In another preferred embodiment, the biocompatible membrane comprises 10 through holes per $mm^2$ of membrane, each with a cross-sectional area of 1800 $\mu m^2$, is 150 $\mu m$ thick, consists of polycaprolactone and is biodegradable, wherein the cross-sectional area of the through holes increases or decreases with a slope of 0.2-0.5 (300-2,000 $\mu m^2$ increase or decrease in cross-sectional area in each 100 $\mu m$ of the membrane's thickness) and at least some of the through holes confine an angle of between 65-89 degrees with the upper surface of the membrane.

In another preferred embodiment, the biocompatible membrane comprises 10 through holes per $mm^2$ of membrane, each with a cross-sectional area of 1800 $\mu m^2$, is 150 $\mu m$ thick, consists of polycaprolactone and is biodegradable, wherein the cross-sectional area of the through holes increases or decreases with a slope of 0.2-0.5 (300-2,000 $\mu m^2$ increase or decrease in cross-sectional area in each 100 $\mu m$ of the membrane's thickness), at least some of the through holes confine an angle of between 65-89 degrees with the upper surface of the membrane, and the membrane comprises mesenchymal stem cells adhered thereto.

In another preferred embodiment, the biocompatible membrane consists of polycaprolactone, is biodegradable and is 150 $\mu m$ thick and comprises 10 through holes per $mm^2$ membrane in the load bearing region section and each of the through holes defines a cross-sectional area of 1200 $\mu m^2$, 4 through holes per $mm^2$ membrane in the non-load bearing region section and each of the through holes defines a cross-sectional area of 1800 $\mu m^2$, and 6 through holes per $mm^2$ membrane in the peripheral rim section and each of the through holes defines a cross-sectional area of 3500 $\mu m^2$, wherein at least some of the through holes confine an angle with the upper surface of the membrane of between 65-89 degrees.

In another preferred embodiment, the biocompatible membrane consists of polycaprolactone, is biodegradable and 150 $\mu m$ thick and comprises 10 through holes per $mm^2$ membrane in the load bearing region section and each of the through holes defines a cross-sectional area of 1200 $\mu m^2$, 4 through holes per $mm^2$ membrane in the non-load bearing region section and each of the through holes defines a cross-sectional area of 1800 $\mu m^2$, and 6 through holes per $mm^2$ membrane in the peripheral rim section and each of the through holes defines a cross-sectional area of 3500 $\mu m^2$, wherein the cross-sectional area of the through holes increases or decreases with a slope of 0.2-0.5 (300-2,000

µm² increase or decrease in cross-sectional area in each 100 µm of the membrane thickness), wherein at least some of the through holes confine an angle with the upper surface of the membrane of between 65-89 degrees.

Implant

An implant of the present invention comprises through holes, also called microchannels. In a preferred embodiment, the implant is biocompatible. In a preferred embodiment, the implant comprises 20 or less though holes or microchannels per mm² of implant surface.

Preferably, the implant is a joint implant. In some embodiments, the implant is a hip, knee, elbow, or shoulder implant. Most preferably, the implant is a hip or knee implant.

As described above for a membrane, which constitutes a particular implant type, an implant of the invention comprises a plurality of through holes. The through holes are also called microchannels and provide for a continuous opening within the implant connecting the base (bone facing) surface with the upper (synovium facing) surface.

The through holes may be arranged perpendicularly (90 degrees) to the surface of the implant. In other embodiments, the through holes are arranged at an angle to the surface of the implant, which is beneficial to mimic the microstructure of the healthy SB. The through holes may then confine an angle of between 1-89 degrees with the surface of the implant. In some embodiments, the through holes confine an angle of between 20-89 degrees with the surface of the implant. In some embodiments, the through holes confine an angle of between 45-89 degrees with the surface of the implant. In some embodiments, the through holes confine an angle of between 45-70 degrees with the surface of the implant. In a preferred embodiment, the through holes confine an angle of between 65-89 degrees with the surface of the implant. Exemplary angles are 65, 70, 75, 80, 85, 89 degrees.

The through holes of the implant may further be arranged identically to one another in their opening-to-opening direction. In some embodiments, the through holes of the implant are arranged differently to one another in their opening-to-opening direction. In some embodiments, some of the through holes are perpendicular to the surface of the implant and others may confine an angle of between 1-89 degrees with the surface of the implant.

The through holes may be arranged in a specific pattern within the implant. In some embodiments, the through holes are arranged on the implant such that the distances between them are identical. In some embodiments, the plurality of through holes is arranged along a gradient with only a few though holes in one portion of the implant and significantly more through holes in one or more other portion of the implant. In other embodiments, the through holes are arranged not in a specific pattern within the implant, but are dispersed randomly within the implant.

The number of through holes within the implant may be specifically defined. In some embodiments, the implant comprises no more than 5, 6, 7, 8, 9, 10, 11, 12, 13, 14, 15, 16, 17, 18, 19, or 20 through holes per mm² of implant surface. In some embodiments, the implant comprises 20 or less through holes per mm² of implant surface. In another embodiment, the implant comprises 10 or less through holes per mm² of implant surface. In another embodiment, the implant comprises between 5 and 15 through holes per mm² of implant surface. In preferred embodiments, the implant comprises 10 through holes per mm² of implant surface.

Further, in some embodiments, each through hole defines a cross-sectional area of between 800 and 4000 µm². In preferred embodiments, each through hole defines a cross-sectional area of between 1200 and 2500 µm². In more preferred embodiments, each through hole defines a cross-sectional area of between 1600 and 1800 µm². In even more preferred embodiments, each through hole defines a cross-sectional area of 1800 µm².

In one exemplary embodiment, each through hole defines a cross-sectional area of around 1000 µm². In one exemplary embodiment, each through hole defines a cross-sectional area of around 1500 µm². In one exemplary embodiment, each through hole defines a cross-sectional area of around 1600 µm². In one exemplary embodiment, each through hole defines a cross-sectional area of around 1700 µm². In one exemplary embodiment, each through hole defines a cross-sectional area of around 1800 µm². In one exemplary embodiment, each through hole defines a cross-sectional area of around 1900 µm². In one exemplary embodiment, each through hole defines a cross-sectional area of around 2000 µm². In one exemplary embodiment, each through hole defines a cross-sectional area of around 2500 µm². In one exemplary embodiment, each through hole defines a cross-sectional area of around 3000 µm². In one exemplary embodiment, each through hole defines a cross-sectional area of around 3500 µm². In one exemplary embodiment, each through hole defines a cross-sectional area of around 4000 µm².

In some embodiments, the implant comprises less than 20 through holes per mm² of implant surface, each defining a cross-sectional area of between 1200 and 2500 µm². In some embodiments, the implant comprises less than 20 through holes per mm² of implant, each with a cross-sectional area of between 1200 and 2500 µm², wherein at least some of the through holes confine an angle with the upper surface of the implant of between 65-89 degrees. In another embodiment, the implant comprises less than 20 through holes per mm² of implant surface, each defining a cross-sectional area of 2500 µm². In some embodiments, the implant comprises less than 20 through holes per mm² of implant, each with a cross-sectional area of 2500 µm², wherein at least some of the through holes confine an angle with the upper surface of the implant of between 65-89 degrees. In another embodiment, the implant comprises less than 20 through holes per mm² of implant, each with a cross-sectional area of 1800 µm². In some embodiments, the implant comprises less than 20 through holes per mm² of implant, each with a cross-sectional area of 1800 µm², wherein at least some of the through holes confine an angle with the upper surface of the implant of between 65-89 degrees. In another embodiment, the implant comprises less than 20 through holes per mm² of implant surface, each defining a cross-sectional area of 1200 µm². In some embodiments, the implant comprises less than 20 through holes per mm² of implant, each with a cross-sectional area of 1200 µm², wherein at least some of the through holes confine an angle with the upper surface of the implant of between 65-89 degrees.

In some embodiments, the implant comprises less than 10 through holes per mm² of implant surface, each defining a cross-sectional area of between 1200 and 2500 µm². In some embodiments, the implant comprises less than 10 through holes per mm² of implant, each with a cross-sectional area of between 1200 and 2500 µm², wherein at least some of the through holes confine an angle with the upper surface of the implant of between 65-89 degrees. In another embodiment, the implant comprises less than 10 through holes per mm² of implant surface, each defining a cross-sectional area of 2500 µm². In some embodiments, the implant comprises less than 10 through holes per mm² of implant, each with a cross-sectional area of 2500 µm², wherein at least some of the through holes confine an angle with the upper surface of the implant of between 65-89 degrees. In another embodiment, the implant comprises less than 10 through holes per mm$^2$ of implant, each with a cross-sectional area of 1800 μm$^2$. In some embodiments, the implant comprises less than 10 through holes per mm$^2$ of implant, each with a cross-sectional area of 1800 μm$^2$, wherein at least some of the through holes confine an angle with the upper surface of the implant of between 65-89 degrees. In another embodiment, the implant comprises less than 10 through holes per mm$^2$ of implant surface, each defining a cross-sectional area of 1200 μm$^2$. In some embodiments, the implant comprises less than 10 through holes per mm$^2$ of implant, each with a cross-sectional area of 1200 μm$^2$, wherein at least some of the through holes confine an angle with the upper surface of the implant of between 65-89 degrees.

In another embodiment, the implant comprises between 10 and 20 through holes per mm$^2$ of implant surface, each defining a cross-sectional area of between 1200 and 2500 μm$^2$. In some embodiments, the implant comprises between 10 and 20 through holes per mm$^2$ of implant, each with a cross-sectional area of between 1200 and 2500 μm$^2$, wherein at least some of the through holes confine an angle with the upper surface of the implant of between 65-89 degrees. In another embodiment, the implant comprises between 10 and 20 through holes per mm$^2$ of implant surface, each defining a cross-sectional area of 2500 μm$^2$. In some embodiments, the implant comprises between 10 and 20 through holes per mm$^2$ of implant, each with a cross-sectional area of 2500 μm$^2$, wherein at least some of the through holes confine an angle with the upper surface of the implant of between 65-89 degrees. In another embodiment, the implant comprises between 10 and 20 through holes per mm$^2$ of implant, each with a cross-sectional area of 1800 μm$^2$. In some embodiments, the implant comprises between 10 and 20 through holes per mm$^2$ of implant, each with a cross-sectional area of 1800 μm$^2$, wherein at least some of the through holes confine an angle with the upper surface of the implant of between 65-89 degrees. In another embodiment, the implant comprises between 10 and 20 through holes per mm$^2$ of implant surface, each defining a cross-sectional area of 1200 μm$^2$. In some embodiments, the implant comprises between 10 and 20 through holes per mm$^2$ of implant, each with a cross-sectional area of 1200 μm$^2$, wherein at least some of the through holes confine an angle with the upper surface of the implant of between 65-89 degrees.

In another embodiment, the implant comprises between 5 and 15 through holes per mm$^2$ of implant surface, each defining a cross-sectional area of between 1200 and 2500 μm$^2$. In some embodiments, the implant comprises between 5 and 15 through holes per mm$^2$ of implant, each with a cross-sectional area of between 1200 and 2500 μm$^2$, wherein at least some of the through holes confine an angle with the upper surface of the implant of between 65-89 degrees. In another embodiment, the implant comprises between 5 and 15 through holes per mm$^2$ of implant surface, each defining a cross-sectional area of 2500 μm$^2$. In some embodiments, the implant comprises between 5 and 15 through holes per mm$^2$ of implant, each with a cross-sectional area of 2500 μm$^2$, wherein at least some of the through holes confine an angle with the upper surface of the implant of between 65-89 degrees. In another embodiment, the implant comprises between 5 and 15 through holes per mm$^2$ of implant, each with a cross-sectional area of 1800 μm$^2$. In some embodiments, the implant comprises between 5 and 15 through holes per mm$^2$ of implant, each with a cross-sectional area of 1800 μm$^2$, wherein at least some of the through holes confine an angle with the upper surface of the implant of between 65-89 degrees. In another embodiment, the implant comprises between 5 and 15 through holes per mm$^2$ of implant surface, each defining a cross-sectional area of 1200 μm$^2$. In some embodiments, the implant comprises between 5 and 15 through holes per mm$^2$ of implant, each with a cross-sectional area of 1200 μm$^2$, wherein at least some of the through holes confine an angle with the upper surface of the implant of between 65-89 degrees.

In a preferred embodiment, the implant comprises 10 through holes per mm$^2$ of implant surface, each defining a cross-sectional area of between 1200 and 2500 μm$^2$. In preferred embodiments, the implant comprises 10 through holes per mm$^2$ of implant, each with a cross-sectional area of between 1200 and 2500 μm$^2$, wherein at least some of the through holes confine an angle with the upper surface of the implant of between 65-89 degrees. In an even more preferred embodiment, the implant comprises 10 through holes per mm$^2$ of implant, each defining a cross-sectional area of 1800 μm$^2$. In another even more preferred embodiments, the implant comprises 10 through holes per mm$^2$ of implant, each with a cross-sectional area of 1800 μm$^2$, wherein at least some of the through holes confine an angle with the upper surface of the implant of between 65-89 degrees.

In another embodiment, the implant comprises 10 through holes per mm$^2$ of implant, each with a cross-sectional area of 1200 μm$^2$. In another embodiment, the implant comprises 10 through holes per mm$^2$ of implant, each with a cross-sectional area of 1200 μm$^2$, wherein at least some of the through holes confine an angle with the upper surface of the implant of between 65-89 degrees.

The through holes may further be arranged on the implant in a pattern of size and distribution (number of through holes per mm$^2$ implant) to substantially match the healthy subchondral bone microarchitecture. Thus, corresponding to subchondral bone, the implant may be divided in distinct sections, i.e. load bearing region, non-load bearing region and peripheral rim (Examples 1 and 2).

The implant may then comprise a specific number of specifically sized through holes in one or more of these sections. In some embodiments, the implant comprises through holes in the load bearing region section that each define a cross-sectional area of between 800 and 1600 μm$^2$. In some embodiments, the implant comprises through holes in the load bearing region section that each define a cross-sectional area of 1200 μm$^2$. In some embodiments, the implant comprises through holes in the non-load bearing region section that each define a cross-sectional area of between 1600 and 2500 μm$^2$. In some embodiments, the implant comprises through holes in the non-load bearing region section that each define a cross-sectional area of 1800 μm$^2$. In some embodiments, the implant comprises through holes in the peripheral rim section that each define a cross-sectional area of between 2500 and 4000 μm$^2$. In some embodiments, the implant comprises through holes in the peripheral rim section that each define a cross-sectional area of 3500 μm$^2$. In some embodiments, the implant comprises 5-15 through holes per mm$^2$ implant in the load bearing region section. In preferred embodiments, the implant comprises 10 through holes per mm$^2$ implant in the load bearing region section. In some embodiments, the implant comprises 2-6 through holes per mm$^2$ implant in the non-load bearing region section. In preferred embodiments, the implant comprises 4 through holes per mm$^2$ implant in the non-load bearing region. In some embodiments, the implant comprises 4-8 through holes per mm$^2$ implant in the peripheral rim section. In preferred embodiments, the implant comprises 6 through holes per mm² implant in the peripheral rim section. In even more preferred embodiments, the implant comprises 10 through holes per mm² implant in the load bearing region section and each of the through holes defines a cross-sectional area of 1200 µm², 4 through holes per mm² implant in the non-load bearing region section and each of the through holes defines a cross-sectional area of 1800 µm², and 6 through holes per mm² implant in the peripheral rim section and each of the through holes defines a cross-sectional area of 3500 µm².

In some embodiments, the implant comprises 10 through holes per mm² implant in the load bearing region section and each of the through holes defines a cross-sectional area of 1200 µm², 4 through holes per mm² implant in the non-load bearing region section and each of the through holes defines a cross-sectional area of 1800 µm², and 6 through holes per mm² implant in the peripheral rim section and each of the through holes defines a cross-sectional area of 3500 µm², wherein at least some of the through holes confine an angle with the upper surface of the implant of between 65-89 degrees.

In some embodiments, the cross-sectional area of the through holes is constant throughout the implant. In some embodiments, the cross-sectional area of at least some of the through holes increases or decreases by up to 50% throughout the implant, compared to the cross-sectional area of the respective through hole at a surface of the implant. In some embodiments, the cross-sectional area increases or decreases with a slope of 0.1-0.2 (i.e. 75-300 µm² increase or decrease in cross-sectional area in each 100 µm of the implant thickness). In other embodiments, the cross-sectional area of the through holes increases or decreases with a slope of 0.5-0.75 (2,000-4,500 µm² increase or decrease in cross-sectional area in each 100 µm of the implant thickness). In preferred embodiments, the cross-sectional area of the through holes increases or decreases with a slope of 0.2-0.5 (300-2,000 µm² increase or decrease in cross-sectional area in each 100 µm of the implant thickness).

In further embodiments, the permeability of the implant comprising a plurality of through holes may be similar to the permeability of a subject's healthy subchondral bone permeability. The permeability of the implant comprising a plurality of through holes may have at least 50%, at least 60%, at least 70%, at least 80%, at least 90%, at least 95% of the permeability of a subject's healthy subchondral bone. In a preferred embodiment, the permeability of the implant comprising a plurality of through holes is identical to that of a subject's healthy subchondral bone permeability. In some embodiments, the permeability of the implant comprising a plurality of through holes may be higher than the permeability of a subject's healthy subchondral bone. The permeability of the implant comprising a plurality of through holes may have at most 105%, at most 110%, at most 120%, at most 130%, at most 140%, at most 150% of the permeability of a subject's healthy subchondral bone.

The implant may further be defined by its thickness. Thus, the implant may be between 50-150 µm thick. In some embodiments, the thickness of the implant is between 50-100 µm. In some embodiments, the thickness of the implant is between 100-150 µm. In preferred embodiments, the thickness of the implant is 150 µm.

In some embodiments, the implant comprises one or more of a metal (such as titanium, implantable steel, or gold), ceramics, plastics, biological materials, hydroxyapatite (HA), tri-calcium-phosphate (TCP), bioactive glasses, polycaprolactone (PCL), or cells. In preferred embodiments, the implant comprises titanium or polycaprolactone. In some embodiments, the implant consists of one or more of a metal (such as titanium, implantable steel, or gold), ceramics, plastics, biological materials, hydroxyapatite (HA), tri-calcium-phosphate (TCP), bioactive glasses, polycaprolactone (PCL), or cells. In preferred embodiments, the implant consists of titanium or polycaprolactone.

In some embodiments, the implant comprises more than one layer. In some embodiments, the implant comprises more than two layers. In some embodiments, one or more layer of the implant is selected from the group of consisting of metals (such as titanium, implantable steel, and gold), ceramics like hydroxyapatite (HA), tri-calcium-phosphate (TCP) or bioactive glasses, polymers, preferably polycaprolactones, biological materials, or cells.

Alternatively, the implant can be manufactured without through holes and these can be introduced by using one or more of a microdrill, a laser ablation system or a water jet. In some embodiments, an implant already containing through holes is manufactured by 3D printing.

In some embodiments, the implant further comprises cells adhered thereto. Cells adhered to the implant may be selected from mesenchymal stem cells, chondrocytes, osteoblasts, osteoclasts, osteoprogenitors, bone lining cells, osteocytes, induced pluripotent cells, genetically modified cells. In preferred embodiments, the implant comprises mesenchymal stem cells adhered thereto.

In preferred embodiments, the implant is biocompatible.

In a preferred embodiment, the implant comprises 10 through holes per mm² of implant, each with a cross-sectional area of 1800 µm², is 150 µm thick, and comprises titanium or polycaprolactone.

In another preferred embodiment, the implant comprises 10 through holes per mm² of implant, each with a cross-sectional area of 1800 µm², is 150 µm thick, comprises titanium or polycaprolactone and is biocompatible, wherein the cross-sectional area of the through holes increases or decreases with a slope of 0.2-0.5 (300-2,500 µm² increase or decrease in cross-sectional area in each 100 µm of the implant thickness).

In another preferred embodiment, the implant comprises 10 through holes per mm² of implant, each with a cross-sectional area of 1800 µm², is 150 µm thick, comprises titanium or polycaprolactone and is biocompatible, wherein the cross-sectional area of the through holes increases or decreases with a slope of 0.2-0.5 (300-2,000 µm² increase or decrease in cross-sectional area in each 100 µm of the implant thickness) and at least some of the through holes confine an angle of between 65-89 degrees with the upper surface of the implant.

In another preferred embodiment, the implant comprises 10 through holes per mm² of implant, each with a cross-sectional area of 1800 µm², is 150 µm thick, comprises titanium or polycaprolactone and is biocompatible, wherein the cross-sectional area of the through holes increases or decreases with a slope of 0.2-0.5 (300-2,000 µm² increase or decrease in cross-sectional area in each 100 µm of the implant thickness), at least some of the through holes confine an angle of between 65-89 degrees with the upper surface of the implant, and the implant comprises mesenchymal stem cells adhered thereto.

In a preferred embodiment, the implant comprises 10 through holes per mm² of implant, each with a cross-sectional area of 1800 µm², is 150 µm thick, and consists of titanium.

In another preferred embodiment, the implant comprises 10 through holes per mm² of implant, each with a cross-sectional area of 1800 µm², is 150 µm thick, consists of titanium and is biocompatible, wherein the cross-sectional area of the through holes increases or decreases with a slope of 0.2-0.5 (300-2,500 µm² increase or decrease in cross-sectional area in each 100 µm of the implant thickness).

In another preferred embodiment, the implant comprises 10 through holes per mm² of implant, each with a cross-sectional area of 1800 µm², is 150 µm thick, consists of titanium and is biocompatible, wherein the cross-sectional area of the through holes increases or decreases with a slope of 0.2-0.5 (300-2,000 µm² increase or decrease in cross-sectional area in each 100 µm of the implant thickness) and at least some of the through holes confine an angle of between 65-89 degrees with the upper surface of the implant.

In another preferred embodiment, the implant comprises 10 through holes per mm² of implant, each with a cross-sectional area of 1800 µm², is 150 µm thick, consists of titanium and is biocompatible, wherein the cross-sectional area of the through holes increases or decreases with a slope of 0.2-0.5 (300-2,000 µm² increase or decrease in cross-sectional area in each 100 µm of the implant thickness), at least some of the through holes confine an angle of between 65-89 degrees with the upper surface of the implant, and the implant comprises mesenchymal stem cells adhered thereto.

In another preferred embodiment, the biocompatible implant consists of titanium, is 150 µm thick and comprises 10 through holes per mm² implant in the load bearing region section and each of the through holes defines a cross-sectional area of 1200 µm², 4 through holes per mm² implant in the non-load bearing region section and each of the through holes defines a cross-sectional area of 1800 µm², and 6 through holes per mm² implant in the peripheral rim section and each of the through holes defines a cross-sectional area of 3500 µm², wherein at least some of the through holes confine an angle with the upper surface of the implant of between 65-89 degrees.

In another preferred embodiment, the biocompatible implant consists of titanium, is 150 µm thick and comprises 10 through holes per mm² implant in the load bearing region section and each of the through holes defines a cross-sectional area of 1200 µm², 4 through holes per mm² implant in the non-load bearing region section and each of the through defines a cross-sectional area of 1800 µm², and 6 through holes per mm² implant in the peripheral rim section and each of the through holes defines a cross-sectional area of 3500 µm², wherein the cross-sectional area of the through holes increases or decreases with a slope of 0.2-0.5 (300-2,000 µm² increase or decrease in cross-sectional area in each 100 µm of the implant thickness), wherein at least some of the through holes confine an angle with the upper surface of the implant of between 65-89 degrees.

Method of Diagnosing the Health State of a Joint of a Subject

The present invention also provides a method of diagnosing the health state of a joint. The method comprises determining the number of microchannels in a region of subchondral bone tissue in a joint, determining the average size of the microchannels of the subchondral bone tissue, comparing the number of microchannels and their size in the subchondral bone tissue with reference data obtained from a corresponding healthy joint or with one or more measurements of the joint of the patient measured at an earlier time point, and determining the health state of the subject's joint based on the number of microchannels and the average size of the microchannels.

The method of diagnosing the health state of a joint of a subject comprises the following steps, a step a) determining the number of microchannels present in subchondral tissue of a subject; a step b) determining the average size of the microchannels of subchondral bone tissue; a step c) comparing data obtained in steps a) and b) with reference data; and a step d) determining, on the basis of step c), the health state of the joint. Additional technical detail relating to each of the disclosed methods steps is provided below.

Method Step a)

In method step a), the number of microchannels present in subchondral tissue in a joint of a subject is determined. In some embodiments, the microchannel analysis can be performed in vivo. In some embodiments, the analysis is performed invasively. In some such embodiments, the analysis is performed via the introduction of a sensor into the joint space. In other embodiments, the analysis is performed non-invasively. In some embodiments, the analysis is performed ex vivo using, for example, conventional imaging techniques. The imaging method for determining the number of channels from outside the body may be high resolution CT analysis, light microscopy, light-sheet microscopy, optical coherence microscopy, high resolution MRI, ultrasound, optoacoustic microscopy. In some of these embodiments, biopsies may be obtained prior to imaging analysis.

Method Step b)

In method step b), the average size of the microchannels of the subchondral bone tissue of the subject is determined. In this respect, the term "size" refers to the cross-sectional area of the microchannel. Similar to the determination of the number of microchannels, this analysis may be carried out invasively or non-invasively from outside the body of the subject. In invasive embodiments, the analysis may be performed via the introduction of a sensor into the joint space. In non-invasive embodiments, the analysis may be performed via imaging from outside the body, including one or more of the following imaging methods: high resolution CT analysis, light microscopy, light-sheet microscopy, optical coherence microscopy, high resolution MRI, ultrasound, optoacoustic microscopy. Some of these imaging methods may also be performed on biopsies be obtained before imaging analysis.

Method Step c)

In method step c), the data obtained in preceding steps a) and b) relating to the number and size of the microchannels present in the subchondral bone tissue of a joint of a subject is compared to corresponding reference data. In this respect, the step of comparing data means evaluating whether the number of microchannels within the subject's subchondral bone tissue significantly deviates from the number of channels present in corresponding healthy reference tissue, and analyzing whether the size of the microchannels within the subject's subchondral bone tissue significantly deviates from the size of the microchannels present in corresponding healthy reference tissue. In some embodiments, the reference tissue is healthy subchondral bone tissue analyzed for microchannel number and size. In some such embodiments, analysis of reference healthy subchondral bone tissue is performed on healthy subjects. In some embodiments, data on reference tissue is obtained from a database. In another embodiment, the corresponding reference tissue is the subject's own healthy tissue, such as a healthy knee of the subject, for instance, when the subject's other knee health state should be assessed. In some embodiments, the corresponding reference tissue is the joint to be assessed, but at an earlier time point.

Method Step d)

In method step d), the health state of the analyzed joint is determined according to the data result obtained from step c), wherein this data is evaluated according to a standard based on a number of microchannels in the load bearing region of the joint of between 0 and 6 per $mm^2$ or 15 per $mm^2$ and more than 15 per $mm^2$, and/or an average size of the microchannels of between 0 and 800 $\mu m^2$ or 10,000 and above 10,000 $\mu m^2$ indicates joint damage. In some embodiments, a number of microchannels in the load-bearing region of the joint between 0 and 6 per $mm^2$ or 15 per $mm^2$ and more than 15 per $mm^2$ indicates joint damage. In some embodiments, an average size of the microchannels between 0 and 800 $\mu m^2$ or 14,000 and above 14,000 $\mu m^2$ indicates joint damage. In some embodiments, a number of microchannels in the load bearing region of the joint between 0 and 6 per $mm^2$ or 15 per $mm^2$ and more than 15 per $mm^2$ and an average size of the microchannels between 0 and 800 $\mu m^2$ or 14,000 and above 14,000 $\mu m^2$ indicates joint damage.

In some embodiments, joint damage indicates the onset of joint-related diseases. In some embodiments, joint damage indicates a risk for the development of joint related diseases, such as osteoarthritis.

In the methods described herein, the subject may be a mammal. In some embodiments, a subject is selected from one of the following: humans, dogs, cats, cows, horses, donkeys, mules, pigs, goats, mice, guinea pigs, and camels. In preferred embodiments, the subject is human.

In some embodiments, the subject is assumed to have or to develop a cartilage destructive disease. A cartilage destructive disease may be selected from osteoarthritis, traumatic joint changes, genetic joint disorders, and joint disorders due to overloading or underloading. In preferred embodiments, the subject is assumed to have or to develop osteoarthritis.

In some embodiments, the joint is selected from a joint of the knee, hip, spine, finger, thumb, neck, or large toe. In preferred embodiments, the joint is a knee joint or a hip joint.

Methods of Treating a Joint of a Subject

The methods according to the present invention provide for the treatment of a diseased joint of a subject. In some embodiments, the method comprises introducing through holes into the subchondral bone of the subject and optionally applying a membrane comprising a plurality of through holes to the subchondral bone.

In another embodiment, the method comprises removing diseased subchondral bone tissue from the joint of the subject and replacing removed tissue with a membrane or an implant comprising a plurality of holes. In preferred embodiments of the invention, the through holes comprised by the membrane or the implant are present in an amount of 20 or less through holes per $mm^2$ membrane or implant surface, respectively. In some embodiments, the subject is a human. In some preferred embodiments, the joint is a knee joint.

A first method of treating a joint of a subject comprises the following steps, a step a) introducing through holes into the subchondral bone; and optionally a step b) applying a membrane comprising a plurality of through holes to the subchondral bone.

Method Step a)

In method step a), through holes are introduced into the subchondral bone of the subject. In some embodiments, the through holes that are introduced into the subchondral bone of the subject have the same dimension and orientation as those comprised by a membrane of the invention. Thus, the through holes may be introduced perpendicularly to the upper (joint facing) surface of the subchondral bone of a subject. In other embodiments, the through are introduced at an angle to the upper surface of the subchondral bone, which is beneficial to mimic the healthy microstructure of the SB. The through holes may then confine an angle of between 1-89 degrees with the upper surface of the subchondral bone. In some embodiments, the through holes confine an angle of between 20-89 degrees with the upper surface of the subchondral bone. In some embodiments, the through holes confine an angle of between 45 and 89 degrees with the upper surface of the subchondral bone. In some embodiments, the through holes confine an angle of between 45-70 degrees with the upper surface of the subchondral bone. In preferred embodiments, the through holes confine an angle of between 65-89 degrees with the upper surface of the subchondral bone.

In some embodiments, the through holes introduced into the subchondral bone of the subject may be arranged identically to one another, such that all through holes are introduced perpendicularly to the upper surface of the subchondral bone. In some embodiments, the through holes introduced into the subchondral bone of the subject may be arranged differently. In some such embodiments, some through holes are introduced perpendicularly to the upper surface of the subchondral bone and some through holes are introduced at an angle (1-89 degrees) to the upper surface of the subchondral bone. In some embodiments, the through holes are introduced into the subchondral bone such that the through holes confine different angles of between 1-89 degrees with the upper surface of the subchondral bone.

The through holes may be arranged in a specific pattern within the subchondral bone. In some embodiments, the through holes are arranged on the subchondral bone such that the distances between them are identical. In some embodiments, the through holes are arranged along a gradient with only a few through holes in one region of the subchondral bone and significantly more through holes in one or more other regions of the subchondral bone. In other embodiments, the through holes are arranged not in a specific pattern within the subchondral bone, but are dispersed randomly.

The number of through holes may be specifically defined. In some embodiments, the plurality of through holes to be introduced into the subchondral bone of a subject comprises no more than 5, 6, 7, 8, 9, 10, 11, 12, 13, 14, 15, 16, 17, 18, 19, or 20 or through holes per $mm^2$ of subchondral bone surface. In some embodiments, the plurality of through holes comprises 20 or less through holes per $mm^2$ of subchondral bone surface. In another embodiment, the plurality of through holes comprises 10 or less through holes per $mm^2$ of subchondral bone surface. In another embodiment, the plurality of through holes comprises between 5 and 15 through holes per $mm^2$ of subchondral bone surface. In another embodiment, the plurality of through holes comprises 10 through holes per $mm^2$ of subchondral bone surface.

Additionally, in some embodiments, each through hole defines a cross-sectional area of between 800 and 4000 $\mu m^2$. In preferred embodiments, each through hole defines a cross-sectional area of between 1200 and 2500 $\mu m^2$. In another embodiment, each through hole defines a cross-sectional area of around 3500 $\mu m^2$. In more preferred embodiments, each through hole defines a cross-sectional area of 1800 $\mu m^2$.

In some embodiments, the plurality of through holes to be introduced into the subchondral bone of a subject comprises less than 20 through holes per mm² of subchondral bone surface, each with a cross-sectional area of between 1200 and 2500 µm². In some embodiments, the plurality of through holes comprises less than 20 through holes per mm² of subchondral bone surface, each with a cross-sectional area of between 1200 and 2500 µm², wherein at least some of the through holes confine an angle with the upper surface of the subchondral bone of between 65-89 degrees. In another embodiment, the plurality of through holes comprises less than 20 through holes per mm² of subchondral bone surface, each with a cross-sectional area of 2500 µm². In some embodiments, the plurality of through holes comprises less than 20 through holes per mm² of subchondral bone surface, each with a cross-sectional area of 2500 µm², wherein at least some of the through holes confine an angle with the upper surface of the subchondral bone of between 65-89 degrees. In another embodiment, the plurality of through holes comprises less than 20 through holes per mm² of subchondral bone surface, each with a cross-sectional area of 1800 µm². In some embodiments, the plurality of through holes comprises less than 20 through holes per mm² of subchondral bone surface, each with a cross-sectional area of 1800 µm², wherein at least some of the through holes confine an angle with the upper surface of the subchondral bone of between 65-89 degrees. In another embodiment, the plurality of through holes comprises less than 20 through holes per mm² of subchondral bone surface, each with a cross-sectional area of 1200 µm². In some embodiments, the plurality of through holes comprises less than 20 through holes per mm² of subchondral bone surface, each with a cross-sectional area of 1200 µm², wherein at least some of the through holes confine an angle with the upper surface of the subchondral bone of between 65-89 degrees.

In some embodiments, the plurality of through holes comprises less than 10 through holes per mm² of subchondral bone surface, each with a cross-sectional area of between 1200 and 2500 µm². In some embodiments, the plurality of through holes comprises less than 10 through holes per mm² of subchondral bone surface, each with a cross-sectional area of between 1200 and 2500 µm², wherein at least some of the through holes confine an angle with the upper surface of the subchondral bone of between 65-89 degrees. In another embodiment, the plurality of through holes comprises less than 10 through holes per mm² of subchondral bone surface, each with a cross-sectional area of 2500 µm². In some embodiments, the plurality of through holes comprises less than 10 through holes per mm² of subchondral bone surface, each with a cross-sectional area of 2500 µm², wherein at least some of the through holes confine an angle with the upper surface of the subchondral bone of between 65-89 degrees. In another embodiment, the plurality of through holes comprises less than 10 through holes per mm² of subchondral bone surface, each with a cross-sectional area of 1800 µm². In some embodiments, the plurality of through holes comprises less than 10 through holes per mm² of subchondral bone surface, each with a cross-sectional area of 1800 µm², wherein at least some of the through holes confine an angle with the upper surface of the subchondral bone of between 65-89 degrees. In another embodiment, the plurality of through holes comprises less than 10 through holes per mm² of subchondral bone surface, each with a cross-sectional area of 1200 µm². In some embodiments, the plurality of through holes comprises less than 10 through holes per mm² of subchondral bone surface, each with a cross-sectional area of 1200 µm², wherein at least some of the through holes confine an angle with the upper surface of the subchondral bone of between 65-89 degrees.

In some embodiments, the plurality of through holes comprises between 10 and 20 through holes per mm² of subchondral bone surface, each with a cross-sectional area of between 1200 and 2500 µm². In some embodiments, the plurality of through holes comprises between 10 and 20 through holes per mm² of subchondral bone surface, each with a cross-sectional area of between 1200 and 2500 µm², wherein at least some of the through holes confine an angle with the upper surface of the subchondral bone of between 65-89 degrees. In another embodiment, the plurality of through holes comprises between 10 and 20 through holes per mm² of subchondral bone surface, each with a cross-sectional area of 2500 µm². In some embodiments, the plurality of through holes comprises between 10 and 20 through holes per mm² of subchondral bone surface, each with a cross-sectional area of 2500 µm², wherein at least some of the through holes confine an angle with the upper surface of the subchondral bone of between 65-89 degrees. In another embodiment, the plurality of through holes comprises between 10 and 20 through holes per mm² of subchondral bone surface, each with a cross-sectional area of 1800 µm². In some embodiments, the plurality of through holes comprises between 10 and 20 through holes per mm² of subchondral bone surface, each with a cross-sectional area of 1800 µm², wherein at least some of the through holes confine an angle with the upper surface of the subchondral bone of between 65-89 degrees. In another embodiment, the plurality of through holes comprises between 10 and 20 through holes per mm² of subchondral bone surface, each with a cross-sectional area of 1200 µm². In some embodiments, the plurality of through holes comprises between 10 and 20 through holes per mm² of subchondral bone surface, each with a cross-sectional area of 1200 µm², wherein at least some of the through holes confine an angle with the upper surface of the subchondral bone of between 65-89 degrees.

In another embodiment, the plurality of through holes comprises between 5 and 15 through holes per mm² of subchondral bone surface, each with a cross-sectional area of between 1200 and 2500 µm². In some embodiments, the plurality of through holes comprises between 5 and 15 through holes per mm² of subchondral bone surface, each with a cross-sectional area of between 1200 and 2500 µm², wherein at least some of the through holes confine an angle with the upper surface of the subchondral bone of between 65-89 degrees. In another embodiment, the plurality of through holes comprises between 5 and 15 through holes per mm² of subchondral bone surface, each with a cross-sectional area of 2500 µm². In some embodiments, the plurality of through holes comprises between 5 and 15 through holes per mm² of subchondral bone surface, each with a cross-sectional area of 2500 µm², wherein at least some of the through holes confine an angle with the upper surface of the subchondral bone of between 65-89 degrees. In another embodiment, the plurality of through holes comprises between 5 and 15 through holes per mm² of subchondral bone surface, each with a cross-sectional area of 1800 µm². In some embodiments, the plurality of through holes comprises between 5 and 15 through holes per mm² of subchondral bone surface, each with a cross-sectional area of 1800 µm², wherein at least some of the through holes confine an angle with the upper surface of the subchondral bone of between 65-89 degrees. In another embodiment, the plurality of through holes comprises between 5 and 15 through holes per mm² of subchondral bone surface, each with a cross-sectional area of 1200 μm². In some embodiments, the plurality of through holes comprises between 5 and 15 through holes per mm² of subchondral bone surface, each with a cross-sectional area of 1200 μm², wherein at least some of the through holes confine an angle with the upper surface of the subchondral bone of between 65-89 degrees.

In a preferred embodiment, the plurality of through holes comprises 10 through holes per μm² of subchondral bone surface, each with a cross-sectional area of between 1200 and 2500 μm². In preferred embodiments, the plurality of through holes comprises 10 through holes per mm² of subchondral bone surface, each with a cross-sectional area of between 1200 and 2500 μm², wherein at least some of the through holes confine an angle with the upper surface of the subchondral bone of between 65-89 degrees. In an even more preferred embodiment, the plurality of through holes comprises 10 through holes per mm² of subchondral bone surface, each with a cross-sectional area of 1800 μm². In another even more preferred embodiment, the plurality of through holes comprises 10 through holes per mm² of subchondral bone surface, each with a cross-sectional area of 1800 μm², wherein at least some of the through holes confine an angle with the upper surface of the subchondral bone of between 65-89 degrees. In another preferred embodiment, the plurality of through holes comprises 10 through holes per mm² of subchondral bone surface, each with a cross-sectional area of 1200 μm². In another embodiment, the plurality of through holes comprises 10 through holes per mm² of subchondral bone surface, each with a cross-sectional area of 1200 μm², wherein at least some of the through holes confine an angle with the upper surface of the subchondral bone of between 65-89 degrees.

The through holes that are introduced in the subchondral bone may be arranged in a pattern of size and distribution (number of through holes per mm² subchondral bone) to substantially match the healthy subchondral bone microarchitecture. Thus, subchondral bone is divided in distinct sections, i.e. load bearing region, non-load bearing region and peripheral rim (Examples 1 and 2).

A specific number of specifically sized through holes may then be introduced in one or more of these sections. In some embodiments, through holes that each define a cross-sectional area of between 800 and 1600 μm² are introduced in the load-bearing region of the subchondral bone. In some embodiments, through holes that each define a cross-sectional area of 1200 μm² are introduced in the load-bearing region of the subchondral bone. In some embodiments, through holes that each define a cross-sectional area of between 1600 and 2500 μm² are introduced in the non-load bearing region of the subchondral bone. In some embodiments, through holes that each define a cross-sectional area of 1800 μm² are introduced in the non-load bearing region section of the subchondral bone. In some embodiments, through holes that each define a cross-sectional area of between 2500 and 4000 μm² are introduced in the peripheral rim of the subchondral bone. In some embodiments, through holes that each define a cross-sectional area of 3500 μm² are introduced in the peripheral rim of the subchondral bone. In some embodiments, 5-15 through holes per mm² subchondral bone are introduced in the load-bearing region. In preferred embodiments, 10 through hole per mm² subchondral bone are introduced in the load-bearing region. In some embodiments, 2-6 through holes per mm² subchondral bone are introduced in the non-load bearing region. In preferred embodiments, 4 through holes per mm² subchondral bone are introduced in the non-load bearing region. In some embodiments, 4-8 through holes per mm² subchondral bone are introduced in the peripheral rim. In preferred embodiments, 6 through holes per mm² subchondral bone are introduced in the peripheral rim. In even more preferred embodiments, 10 through holes per mm² subchondral bone are introduced in the load bearing region and each of the through holes defines a cross-sectional area of 1200 μm², 4 through holes per mm² subchondral bone are introduced in the non-load bearing region and each of the through holes defines a cross-sectional area of 1800 μm², and 6 through holes per mm² subchondral bone are introduced in the peripheral rim and each of the through holes defines a cross-sectional area of 3500 μm².

In some embodiments, 10 through holes per mm² subchondral bone are introduced in the load bearing region and each of the through holes defines a cross-sectional area of 1200 μm², 4 through holes per mm² subchondral bone are introduced in the non-load bearing region section and each of the through holes defines a cross-sectional area of 1800 μm², and 6 through holes per mm² subchondral bone are introduced in the peripheral rim and each of the through holes defines a cross-sectional area of 3500 μm², wherein at least some of the through holes confine an angle with the upper surface of the subchondral bone of between 65-89 degrees.

In some embodiments, the through holes introduced into subject's subchondral bone have a length of at least 150 μm. In some preferred embodiments, the through holes introduced into subject's subchondral bone have a length of at least 200 μm. In some embodiments, the through holes introduced into subject's subchondral bone have a length of at least 250 μm. In some embodiments, the through holes introduced into subject's subchondral bone have a length of at least 300 μm. In other embodiments, the through holes comprise a length corresponding to the thickness of the subchondral bone of the subject.

In some embodiments, the through holes introduced into subject's subchondral bone form a continuous opening from the upper surface of the subchondral bone of the subject to the underlying trabecular spacings, which contain bone marrow and vascular structures.

In further embodiments, the permeability of a subject's subchondral bone that has been modified by introducing through holes into the bone may be similar to the permeability of the subject's healthy subchondral bone. The permeability of the subchondral bone which has been modified by introducing through holes into the bone may be at least 50%, at least 60%, at least 70%, at least 80%, at least 90%, at least 95% of the permeability of the subject's healthy subchondral bone. In a preferred embodiment, the permeability of the subject's subchondral bone that has been modified by introducing through holes into the bone is identical to the permeability of the subject's healthy subchondral bone. In some embodiments, the permeability of the subject's subchondral bone that has been modified by introducing through holes into the bone may be higher than the permeability of a subject's healthy subchondral bone. The permeability of the membrane comprising a plurality of through holes may have at most 105%, at most 110%, at most 120%, at most 130%, at most 140%, at most 150% of the permeability of a subject's healthy subchondral bone.

In other embodiments, the through holes introduced into the subchondral bone of the subject may resemble in number and size microchannels of healthy subchondral bone. In some such embodiments, the through holes resemble microchannels of healthy reference tissue in number and in average size. In some embodiments, the corresponding reference tissue is obtained from a database. In another embodiment, the corresponding reference tissue is the subject's own healthy tissue, such as a healthy knee of the subject, for instance, when the other knee is intended to be subjected to treatment. In some embodiments, the corresponding reference tissue is the subchondral bone subjected to treatment, but assessed at an earlier time point.

Figure 3:
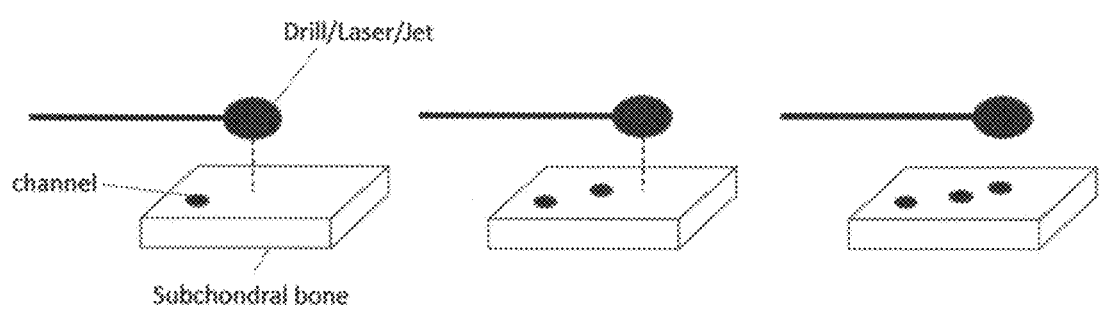
FIG. 3 is a schematic illustrating microchannel formation in subchondral bone according to an embodiment of the invention, wherein 1: through hole/microchannel, 2: subchondral bone, 3: drill/laser/jet.

The through holes may further be introduced into a subject's subchondral bone by one or more of a microdrill, a water jet, or a laser ablation system. In preferred embodiments, the through holes are introduced into subchondral bone by applying a laser ablation system. In some embodiments, through holes are introduced into subchondral bone in parallel. In some embodiments, through holes are introduced into subchondral bone sequentially, as illustrated, for example in FIG. 3.

In preferred embodiments, 10 through holes per $mm^2$ subchondral bone are introduced in the load bearing region section and each of the through holes defines a cross-sectional area of 1200 $\mu m^2$, 4 through holes per $mm^2$ subchondral bone are introduced in the non-load bearing region section and each of the through holes defines a cross-sectional area of 1800 $\mu m^2$, and 6 through holes per $mm^2$ subchondral bone are introduced in the peripheral rim section and each of the through holes defines a cross-sectional area of 3500 $\mu m^2$, wherein at least some of the through holes confine an angle with the upper surface of the subchondral bone of between 65-89 degrees and wherein the through holes introduced into subject's subchondral bone form a continuous opening from the upper surface of the subchondral bone to the underlying vascular system of the subject.

Method Step b)

In method step b), a membrane comprising a plurality of through holes is applied to the subchondral bone of the subject. The membrane comprising through holes according to step b) is a membrane embodied in the present invention, which is described in detail above. In some embodiments, the membrane is applied to the subchondral bone by placing the membrane on top of the upper (joint facing) surface of the subchondral bone of the subject. In some embodiments, the membrane is placed centrally on the upper surface of the subchondral bone of the subject. In some embodiments, the membrane is not placed centrally on the upper surface of the subchondral bone of the subject, but onto diseased regions of the upper surface of the subchondral bone. In the context of the present invention, the diseased regions are those in which the microarchitecture of the subchondral bone has already been changed or damaged due to disease progression of, for example, osteoarthritis.

In some embodiments of the invention, the membrane is additionally affixed to the bony tissue. The membrane may be affixed to the bony tissue via the exemplary affixing means of a screw, glue, nail, or stitches. In some embodiments, affixing using a screw is accomplished with biocompatible screws. Suitable biocompatible screws may comprise implantable steel, gold, titanium, ceramics, and plastics. In other embodiments, affixing using a nail is accomplished with biocompatible nails comprising implantable steel, gold, titanium, ceramics, and plastics. In other embodiments, affixing using stitches may be accomplished with biodegradable or non-biodegradable thread. Thus, stitching may be permanent or non-permanent. In preferred embodiments, the membrane is fixed with glue to the bony tissue. In even more preferred embodiments the glue comprises fibrinogen.

In the methods disclosed above, the subject may be a mammal. In some embodiments, the subject is selected from one of the following: humans, dogs, cats, cows, horses, donkeys, mules, pigs, goats, mice, guinea pigs, and camels. In preferred embodiments, the subject is a human.

In some embodiments, the subject is assumed to have or to develop a cartilage destructive disease. A cartilage destructive disease may be selected from osteoarthritis, traumatic joint changes, genetic joint disorders, joint disorders due to overloading or underloading. In preferred embodiments, the subject is assumed to have or to develop osteoarthritis.

In some embodiments, the joint is selected from a joint of the knee, hip, spine, finger, thumb, neck, or large toe. In preferred embodiments, the joint is a knee joint or a hip joint, in most preferred embodiments, the joint is a knee joint An second method embodiment useful for treating a joint of a subject comprises the following steps, an alternative step a') removing diseased subchondral bone tissue from the joint of a subject; and an alternative step b') inserting a membrane or an implant comprising a plurality of through holes into the subject, thereby replacing the diseased subchondral bone tissue that was removed in step a').

Alternative Method Step a')

In alternative method step a'), diseased subchondral bone tissue is removed from the joint of a subject, the subchondral bone of a subject is prepared for the insertion of an implant. In some embodiments, diseased subchondral bone is removed by ablating damaged tissue by using a burr, a laser, saw or a knife.

Alternative Method Step b')

In alternative method step b'), a membrane an implant is inserted into the subject to replace the tissue removed in step a). The membrane or implant comprising a plurality of through holes to be inserted is a membrane or an implant of the invention, which is defined in technical detail above.

In some embodiments, the membrane or implant is inserted by placing the membrane or implant on top of the bone prepared for the insertion in step a), and affixing the membrane or implant to the bone.

In some embodiments, the membrane or implant is placed centrally on the upper (joint facing) surface of the bone of the subject. In some embodiments, the membrane or implant is not placed centrally on the upper surface of the bone of the subject, but instead onto diseased regions of the upper surface of the bone. In this context, diseased regions refer to those in which the microarchitecture of the subchondral bone has already been changed or damaged due to disease progression of a joint disease, for example, osteoarthritis.

In some embodiments of the invention, the membrane or implant is further affixed to the bony tissue of a subject. The implant may be affixed to the bony tissue via a pin, a screw or glue. In some embodiments, a pin is a biocompatible pin. Suitable biocompatible pins may comprise implantable steel, gold, titanium, ceramics, and plastics. In some embodiments, the affixing using a screw is accomplished with biocompatible screws. Suitable biocompatible screws may comprise implantable steel, gold, titanium, ceramics, and plastics. In preferred embodiments, the implant is fixed with glue to the bony tissue. In even more preferred embodiments the glue comprises cement.

The membrane may be affixed to the bony tissue by an affixing means using a screw, nail, glue or stitches. In some embodiments, affixing using a screw is accomplished with biocompatible screws. Suitable biocompatible screws may comprise implantable steel, gold, titanium, ceramics, and plastics. In other embodiments, affixing using a nail is accomplished with biocompatible nails comprising implantable steel, gold, titanium, ceramics, and plastics. In other embodiments, affixing using stitches may be accomplished with biodegradable or non-biodegradable thread. Thus, stitching may be permanent or non-permanent. In preferred embodiments, the membrane is fixed with glue to the bony tissue. In even more preferred embodiments the glue comprises fibrinogen.

In the methods disclosed herein, the subject may be a mammal. In some embodiments, the subject is selected from one of the following: humans, dogs, cats, cows, horses, donkeys, mules, pigs, goats, mice, guinea pigs, and camels. In preferred embodiments, the subject is a human.

In some embodiments, the subject is assumed to have or to develop a cartilage destructive disease. Exemplary cartilage destructive diseases may be selected from osteoarthritis, traumatic joint changes, genetic joint disorders, joint disorders due to overloading or underloading. In preferred embodiments, the subject is assumed to have or to develop osteoarthritis.

In some embodiments, the joint is selected from a joint of the knee, hip, spine, finger, thumb, neck, or large toe. In preferred embodiments, the joint is a knee joint or a hip joint, most preferably the joint is a knee joint.

ADDITIONAL EMBODIMENTS

Each of the below items corresponds to an additional embodiment of the presently biocompatible membranes and/or implants described and claimed herein.
1. A biocompatible membrane comprising a plurality of through holes, wherein the membrane comprises 20 or less through holes per mm$^2$ of membrane.
2. The biocompatible membrane of embodiment 1, wherein the membrane comprises 10 or less through holes per mm$^2$ of membrane.
3. The biocompatible membrane of embodiment 1, wherein the membrane comprises between 5 and 15 through holes per mm$^2$ of membrane.
4. The biocompatible membrane of embodiment 3, wherein the membrane comprises 10 through holes per mm$^2$ of membrane.
5. The biocompatible membrane of any of the preceding embodiments, wherein each of the plurality of through holes defines a cross-sectional area of between 800 and 4000 µm$^2$.
6. The biocompatible membrane of embodiment 5, wherein each of the plurality of through holes defines a cross-sectional area of between 1200 and 2500 µm$^2$.
7. The biocompatible membrane of embodiment 6, wherein each of the plurality of through holes defines a cross-sectional area of between 1600 and 1800 µm$^2$.
8. The biocompatible membrane of embodiment 1, wherein the through holes are arranged in a size and distribution pattern that correspond to the pattern of microchannels of one or more of the load bearing region, non-load bearing region or peripheral rim of subchondral bone, so that the membrane comprising a plurality of through holes is divided in one or more of a load bearing region section, a non-load bearing region section and/or a peripheral rim section.
9. The biocompatible membrane of embodiment 8, wherein each of the through holes in the load bearing region section defines a cross-sectional area of between 800 and 1600 µm$^2$, each of the through holes in the non-load bearing region section defines a cross-sectional area of between 1600 and 2500 µm$^2$, and each of the through holes in the peripheral rim section defines a cross-sectional area of between 2500 and 4000 µm$^2$.
10. The biocompatible membrane of embodiment 9, wherein the load bearing region section comprises 10 through holes per mm$^2$ membrane and each of the through holes defines a cross-sectional area of 1200 µm$^2$, the non-load bearing region section comprises 4 through holes per mm$^2$ membrane and each of the through holes defines a cross-sectional area of 1800 µm$^2$, and the peripheral rim section comprises 6 through holes per mm$^2$ membrane and each of the through holes defines a cross-sectional area of 3500 µm$^2$.
11. The biocompatible membrane of any of embodiments 1-10, wherein the thickness of the membrane is 50-150 µm.
12. The biocompatible membrane of embodiments 1-11, wherein the thickness of the membrane is 50-100 µm.
13. The biocompatible membrane of embodiments 1-11, wherein the thickness of the membrane is 100-150 µm.
14. The biocompatible membrane of embodiments 1-11, wherein the thickness of the membrane is 150 µm.
15. The biocompatible membrane of any of the preceding embodiments, wherein at least some of the through holes confine an angle of between 65-89 degrees with the surface of the membrane.
16. The biocompatible membrane of any of the preceding embodiments, wherein the cross-sectional area of at least some of the through holes increases or decreases by up to 50% throughout the membrane, compared to the cross-sectional area of the respective through hole at a surface of the membrane.
17. The biocompatible membrane of any of the preceding embodiments, wherein the cross-sectional area of at least some of the through holes increases or decreases with a slope of 0.1-0.2 (75-300 µm$^2$ increase or decrease in cross-sectional area in each 100 µm of the membrane's thickness).
18. The biocompatible membrane of any of the preceding embodiments, wherein the permeability of the membrane corresponds to the permeability of a patient's healthy joint.
19. The biocompatible membrane of any of the preceding embodiments, wherein the membrane comprises polycaprolactone.
20. The biocompatible membrane of any of the preceding embodiments, wherein the membrane consists of polycaprolactone.
21. The biocompatible membrane of any of the preceding embodiments, wherein the membrane comprises more than one layer.
22. The biocompatible membrane of any of the preceding embodiments, wherein the membrane comprises more than two layers.
23. The biocompatible membrane of any of the preceding embodiments, wherein the membrane further comprises cells adhered thereto.
24. The biocompatible membrane of any of the preceding embodiments, wherein the membrane is biodegradable.
25. An implant comprising a plurality of through holes.
26. The implant of embodiment 25, wherein the implant comprises 20 or less through holes per mm$^2$ of implant.
27. The implant of embodiment 25, wherein the implant comprises 10 or less through holes per mm$^2$ of implant.
28. The implant of embodiment 25, wherein the implant comprises between 5 and 15 through holes per mm$^2$ of implant.
29. The implant of embodiment 28, wherein the implant comprises 10 through holes per mm$^2$ of implant.
30. The implant of any of embodiments 25-29, wherein each of the plurality of through holes defines a cross-sectional area of between 800 and 4000 µm$^2$.
31. The implant of embodiment 30, wherein each of the plurality of through holes defines a cross-sectional area of between 1200 and 2500 µm$^2$.

32. The implant of embodiment 31, wherein each of the plurality of through holes defines a cross-sectional area of between 1600 and 1800 µm².

33. The implant of embodiment 25, wherein the through holes are arranged in a size and distribution pattern that correspond to the pattern of microchannels of one or more of the load bearing region, non-load bearing region or peripheral rim of subchondral bone, so that the implant comprising a plurality of through holes is divided in one or more of a load bearing region section, a non-load bearing region section and/or a peripheral rim section.

34. The implant of embodiment 33, wherein each of the through holes in the load bearing region section defines a cross-sectional area of between 800 and 1600 µm², each of the through holes in the non-load bearing region section defines a cross-sectional area of between 1600 and 2500 µm², and each of the through holes in the peripheral rim section defines a cross-sectional area of between 2500 and 4000 µm².

35. The implant of embodiment 34, wherein the load bearing region section comprises 10 through holes per mm² implant and each of the through holes defines a cross-sectional area of 1200 µm², the non-load bearing region section comprises 4 through holes per mm² implant and each of the through holes defines a cross-sectional area of 1800 µm², and the peripheral rim section comprises 6 through holes per mm² implant and each of the through holes defines a cross-sectional area of 3500 µm².

36. The implant of any of embodiments 25-35, wherein at least some of the through holes confine an angle of between 65-89 degrees with the surface of the implant.

37. The implant of any of embodiments 25-36, wherein the cross-sectional area of at least some of the through holes increases or decreases by up to 50% throughout the membrane, compared to the cross-sectional area of the respective through hole at a surface of the membrane.

38. The implant of any of embodiments 25-36, wherein the cross-sectional area of at least some of the through holes increases or decreases with a slope of 0.1-0.2 (75-300 µm² increase or decrease in cross-sectional area in each 100 µm of the implant thickness).

39. The implant of any of embodiments 25-38, wherein the implant comprises more than one layer.

40. The implant of any of embodiments 25-39, wherein the implant comprises more than two layers.

41. The implant of any of embodiments 25-40, wherein the implant further comprises cells adhered thereto.

42. The implant of any of embodiments 25-41, wherein the implant is a hip, knee, elbow, or shoulder implant, preferably the implant is a hip or a knee implant, most preferably a knee implant.

43. The implant of any of embodiments 25-41, wherein the implant comprises one or more of a metal, ceramics, polymer, preferably polycaprolactone, biological materials, hydroxyapatite, cells, or combinations thereof.

44. A method of diagnosing health state of a joint of a subject, the method comprising a) determining the number of microchannels present in subchondral tissue of a subject; b) determining average size of the microchannels of subchondral bone tissue; c) comparing data obtained in steps a) and b) with reference data; d) determining on the basis of c) the health state of the joint; wherein a number of microchannels between 0 and 6 per mm2 or 15 and more than 15 per mm2 in the load bearing region of the joint and/or an average cross-sectional area of the microchannels between 0 and 800 µm2 or 14,000 and above 14,000 µm2 indicate joint damage.

45. The method of embodiment 44, wherein the method is for monitoring destruction of a joint of a subject, and wherein step c) comprises comparing data obtained in step b) with reference data obtained from the same joint at an earlier time point.

46. The method of any of embodiments 44-45, wherein the method is for diagnosing atherosclerosis in a subject.

47. The method of any of embodiments 44-46, wherein the joint is a knee joint.

48. The method of any of embodiments 44-47, wherein the subject is a mammal.

49. The method of embodiment 48, wherein the subject is human.

50. A method of treating a joint of a subject in need thereof, wherein the method comprises 51. a) introducing through holes into the subchondral bone; and optionally 52. b) applying a membrane according to any of embodiments 1-24 to the subchondral bone.

53. The method of embodiment 50, wherein the membrane is fixed by fibrinogen glue to the bony tissue.

54. The method of embodiment 50 or 51, wherein the joint is a knee joint.

55. The method of embodiments 50-52, wherein the subject is a mammal.

56. The method of embodiment 53, wherein the subject is human.

57. The method of any of embodiments 50-54, wherein the through holes introduced in step a) are arranged in a pattern of 20 or less through holes per mm² on the subchondral bone.

58. The method of any of embodiments 50-54, wherein the through holes introduced in step a) are arranged in a pattern of 10 or less through holes per mm² on the subchondral bone.

59. The method of any of embodiments 50-54, wherein the through holes introduced in step a) are arranged in a pattern of between 5 and 15 through holes per mm² on the subchondral bone.

60. The method of embodiment 57, wherein the through holes introduced in step a) are arranged in a pattern of 10 through holes per mm² on the subchondral bone.

61. The method of embodiments 50-54, wherein the through holes introduced in step a) are arranged in a size and distribution pattern that correspond to the pattern of microchannels of one or more of the load bearing region, non-load bearing region or peripheral rim of healthy subchondral bone.

62. The method of embodiment 59, wherein each of the through holes introduced in the load bearing region defines a cross-sectional area of between 800 and 1600 µm², each of the through holes introduced in the non-load bearing region defines a cross-sectional area of between 1600 and 2500 µm², and each of the through holes introduced in the peripheral rim defines a cross-sectional area of between 2500 and 4000 µm².

63. The method of embodiment 60, wherein after step a) the load bearing region comprises 10 through holes per mm² of subchondral bone and each of the through holes defines a cross-sectional area of 1200 µm², the non-load bearing region comprises 4 through holes per mm² of subchondral bone and each of the through holes defines a cross-sectional area of 1800 µm², and the peripheral rim comprises 6 through holes per mm² of subchondral bone and each of the through holes defines a cross-sectional area of 3500 µm².

64. The method of any of embodiments 50-61, wherein the through holes introduced in step a) comprise a length of at least 200 µm measured from the surface of the subchondral bone.
65. The method of any of embodiments 50-61, wherein the through holes introduced in step a) comprise a length corresponding to the thickness of the subchondral bone of the subject.
66. The method of any of embodiments 50-61, wherein the through holes introduced in step a) form a continuous opening from the upper surface of the subchondral bone of the subject to the underlying trabecular spacings.
67. A method of treating a joint of a subject in need thereof, wherein the method comprises a) removing diseased subchondral bone tissue from the joint of the subject; and b) inserting a biocompatible membrane according to any of embodiments 1-24 into the subject thereby replacing the diseased subchondral bone tissue removed in step a).
68. A method of treating a joint of a subject in need thereof, wherein the method comprises a) removing diseased subchondral bone tissue from the joint of the subject; and b) inserting an implant according to any of embodiments 25-43 into the subject thereby replacing the diseased subchondral bone tissue removed in step a).
69. The method of embodiment 65 or embodiment 66, wherein the joint is a knee joint.
70. The method of any of embodiments 65-67, wherein the subject is a mammal.
71. The method of embodiment 68, wherein the subject is human.

Because modifications can be made to the above-described compositions and methods without departing from the scope of the invention, it is intended that the disclosure herein, including examples provided below, shall be interpreted as illustrative, non-limiting aspects of the invention.

EXAMPLES

The following examples are provided for the purposes of illustrating one or more embodiments of the present invention.

Example 1

Healthy human hipbone tissue samples were retrieved from anonymous body donors. The load bearing region (LBR), the non-load bearing region (NLBR), and the peripheral rim (PR) were identified in each of the samples and suitable CT samples (cylindrical specimens that were determined to undergo CT analysis) were obtained. Hipbone CT samples were then analyzed using a micro-CT device.

For identification of the load bearing region, the non-load bearing region, and the rim region, superimposed contact forces of all the participants during normal walking were plotted. In addition, identification of these regions was based on visual inspections of the SB microstructure as well as other reference criteria [1-3].

For accurate sampling of CT samples, 43 measurement points were defined and extracted on each hip sample, as illustrated in FIG. 1A. These points represent the convergence points of two sets of anatomical drawings on the femoral heads: 1) Twelve concentric lines, each separated by a 30 degrees angle interval, which started from the center (C) of the femoral head and ended on the neck junction; 2) four parallel parasagittal planes, dividing the arc between the C and the neck junctions into equally-spaced regions. C was determined as the intersection of the long axis and the coronal plane. The location of the measurement points was standardized using a template grid, taking into consideration the normalized size of each femoral head.

From the total of 43 measurement points, 12 accounted for the load bearing region (LBR), 12 for the non-load bearing region (NLBR), and 19 for the peripheral rim (PR), as illustrated in FIG. 1A.

2.00 mm cylindrical specimens (CT samples) (n: 43*5=215) were then drilled out from each hip sample, using a trephine at the respective measurement points and subjected to micro-CT analysis, as shown in FIG. 1B, FIG. 1C, and FIG. 1D, wherein FIG. 1B depicts the LBR, FIG. 1C depicts the NLBR, and FIG. 1D depicts the PR.

Example 2

Bone extracts obtained in Example 1 were placed into sample holders, and scanned using a micro-CT (µCT 50, SCANCO Medical AG, Switzerland) using the following settings: voxel size=1.2 µm, source voltage=90 kVp, intensity=88 µA, integration time=1500 ms, and 0.5 mm aluminum filter.

The cartilage was distinguished and segmented from the air and bone with the aid of a 3D segmentation script (air: −500--140 mg HA/cm$^3$, cartilage: −140-600 mg HA/cm$^3$, bone: 600-3000 mg HA/cm$^3$, Sigma: 2, Support: 4). The articular cartilage (AC) thickness for each sample was measured at 60 fixed spots within three cross-sections of the model to obtain a mean value. The subchondral bone thickness was measured in a similar fashion after excluding the extensions of the subarticular trabecular bone. The results are shown in FIG. 2A.

For quantification of the microchannels, the scanned models with deviations above 1-degree angles from the XY plane were aligned. They were then binarized, converted to TIFF stacks, and imported into Fiji for analysis. The volume of interest was a 0.07 mm$^2$ cylinder that started from the tidemark and encompassed the entire SB.

Figure 2B:
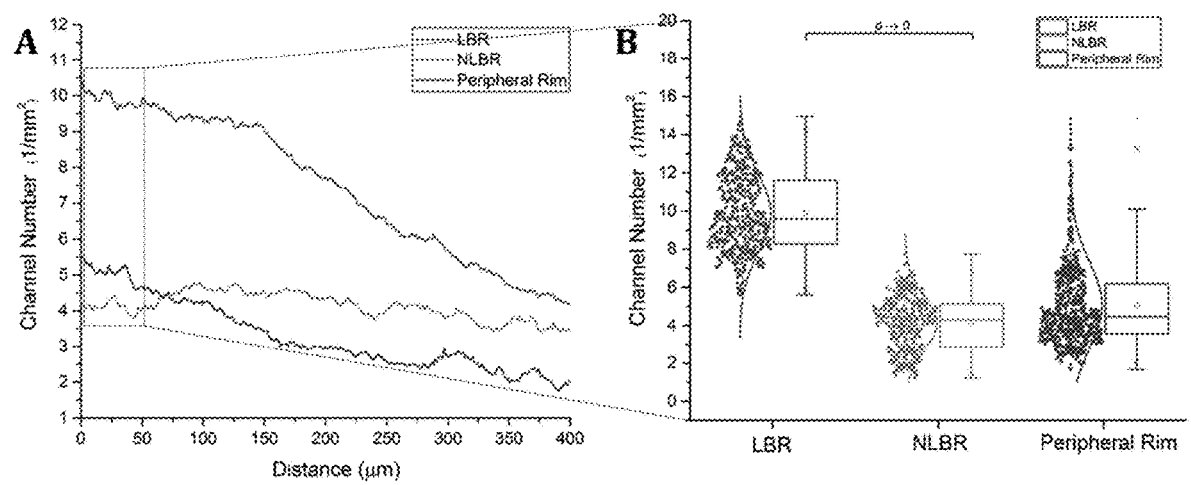

Channel number (Ch.N.) was defined as the number of channels per mm$^2$. The results are shown in FIG. 2B. The size of the microchannels was quantified by Feret, which is defined as the longest distance between any two points along the selection boundary, also known as maximum caliper. Likewise, the minimum caliper diameter (MinFeret) was measured to calculate the shortest distance inside of the channels, see results shown in FIG. 2C. The morphology of the channels was quantified by the circularity (Circ.) index. A circularity value of 1.0 indicates a perfect circle, and as the value approaches 0.0, it indicates an increasingly elongated polygon. See results shown in FIG. 2D.

The measurements are quantified by a macro-based algorithm that calculates the structural parameters of the microchannels on a layer-by-layer basis. For each measurement point, and at any given distance from the tidemark, the parameters are represented by their median values. The final reported numbers are the mean±standard deviation of corresponding layers.

Results:

The present inventors found that the changes of the cartilage and SB thicknesses followed an identified gradient pattern with respect to different regions of the joint. The thickness of the AC was highest at the LBR (809±183 µm), medium at the NLBR (490±148 µm), and lowest at the PR (313±124 µm) of the hip joint, see FIG. 2A at box A, left-hand side. A similar observation was found for the changes of the SB thickness across the joint, as shown in FIG. 2A at box B, right-hand side; LBR=241±79 µm; NLBR=185±78 µm; PR=154±88 µm.

The 3D-reconstructed models of the subchondral bone revealed that the microchannels have a continuous characteristic insofar as the cartilage-bone interface was directly connected to the trabecular bone through this microchannel network. The inventors identified a location-dependent pattern for these channels in the joint: In the load-bearing region (LBR), many small channels reached to the most superficial surface of the SB, and were in direct contact with the basal cartilage, as shown in FIG. 1B. On the other hand, the NLBR was mainly characterized by an intermittent distribution of microchannels, while having a bigger contact size at the top surface of the SB in comparison with the LBR (FIG. 1C). At the peripheral rim (PR) of the femoral head, however, the microarchitecture of the SB was mainly comprised of non-circular channels with the highest channel sizes observed as shown in FIG. 1D. Notably, the channels were more frequent in the peripheral rim compared to the NLBR, but less frequent than in the LBR.

The quantification results are in line with the above-mentioned observations. FIG. 2B shows the profiles of the changes of the mean channel number (Ch.N.; $1/mm^2$) versus distance from the tidemark (D) in different regions of the femoral head. The profiles are distinct throughout the SB, with the LBR having a consistently higher Ch.N. compared to the other two regions. Close to the tidemark, the profiles were either exhibited a slow declining rate (LBR and PR) or were almost constant (NLBR). At increasing distances below the subchondral bone plate (subarticular bone), the slope was much steeper, corresponding to the spacings between the trabeculae. At the cartilage-bone interface, the Ch.N. at the tidemark (D=0) was ≈10, 5.5, and 4, respectively. The box-plot representation of the Ch.N. in the upper 50 µm of the SB revealed a significantly (p→0) higher values in the LBR compared to the NLBR and the PR.

Figure 2C:
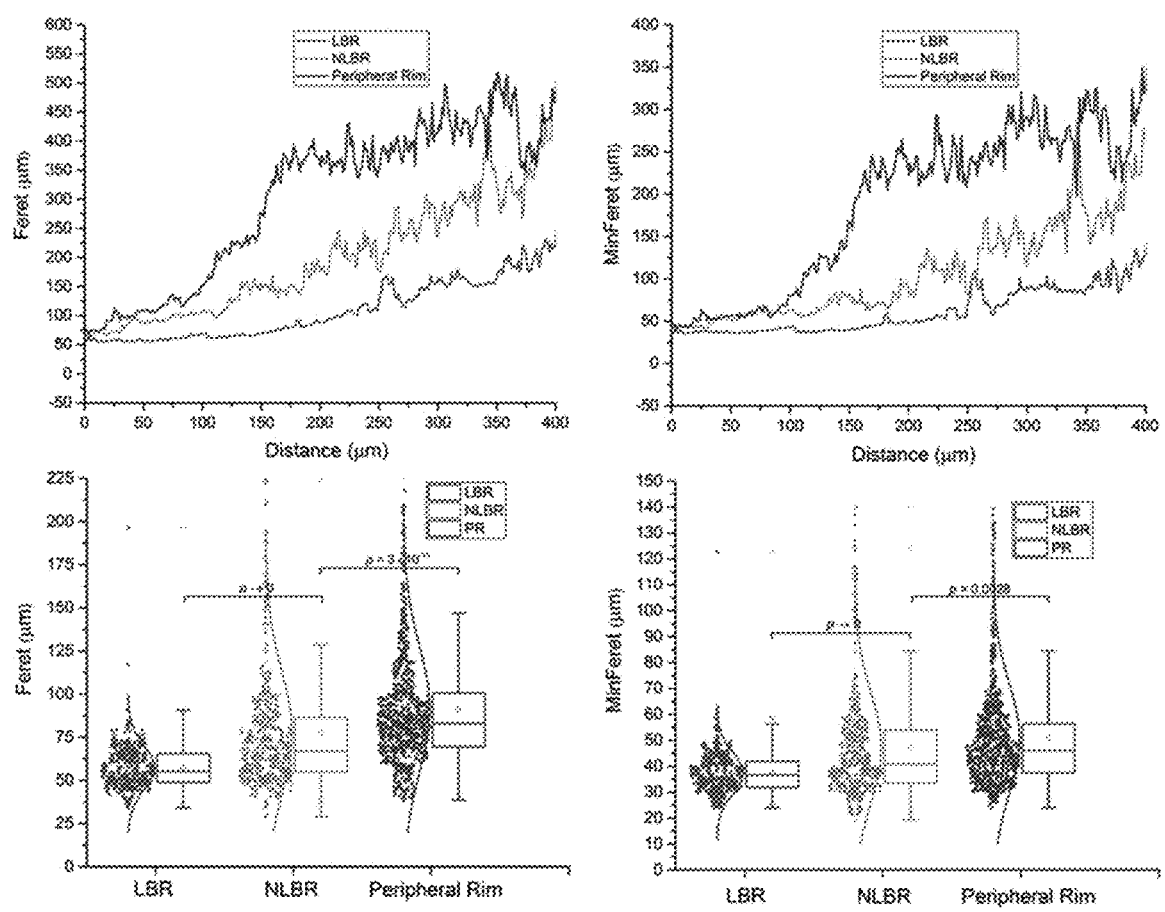

The size distribution of the microchannels in the upper 50 µm of the SB is illustrated by the histograms shown in FIG. 2C. The present inventors found that as the region shifted from the LBR to the PR, the size of the channels progressively increased. A mean Feret diameter of 57.47±13 µm, 77.42±36 µm, and 91.13±36 µm for the LBR, NLBR, and PR, respectively, was observed, in particular, a much higher number of 100 µm microchannels in the PR, which confirmed the macroscopic observations. The MinFeret diameter of the microchannels followed a similar pattern, with statistically significant differences observed between all regions.

Figure 2D:
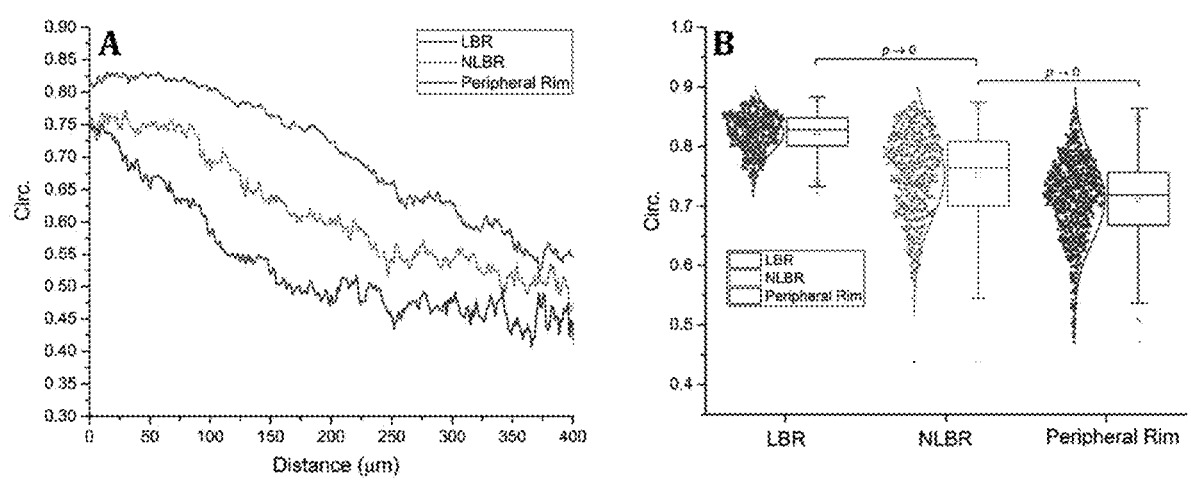

The morphology of the microchannels was also observed to be location-dependent, as shown in FIG. 2D at box A, left-hand side. Close to the tidemark (top 50 µm; see FIG. 2D at box B, right-hand side), the mean values of Circ. were 0.82±0.03, 0.75±0.07, and 0.70±0.07 for the LBR, NLBR, and PR, respectively. Therefore, as the region transitioned from the LBR to the PR, the circularity of the microchannels declined significantly and showed a mixture of asymmetrical and elongated shapes.

Figure 2E:
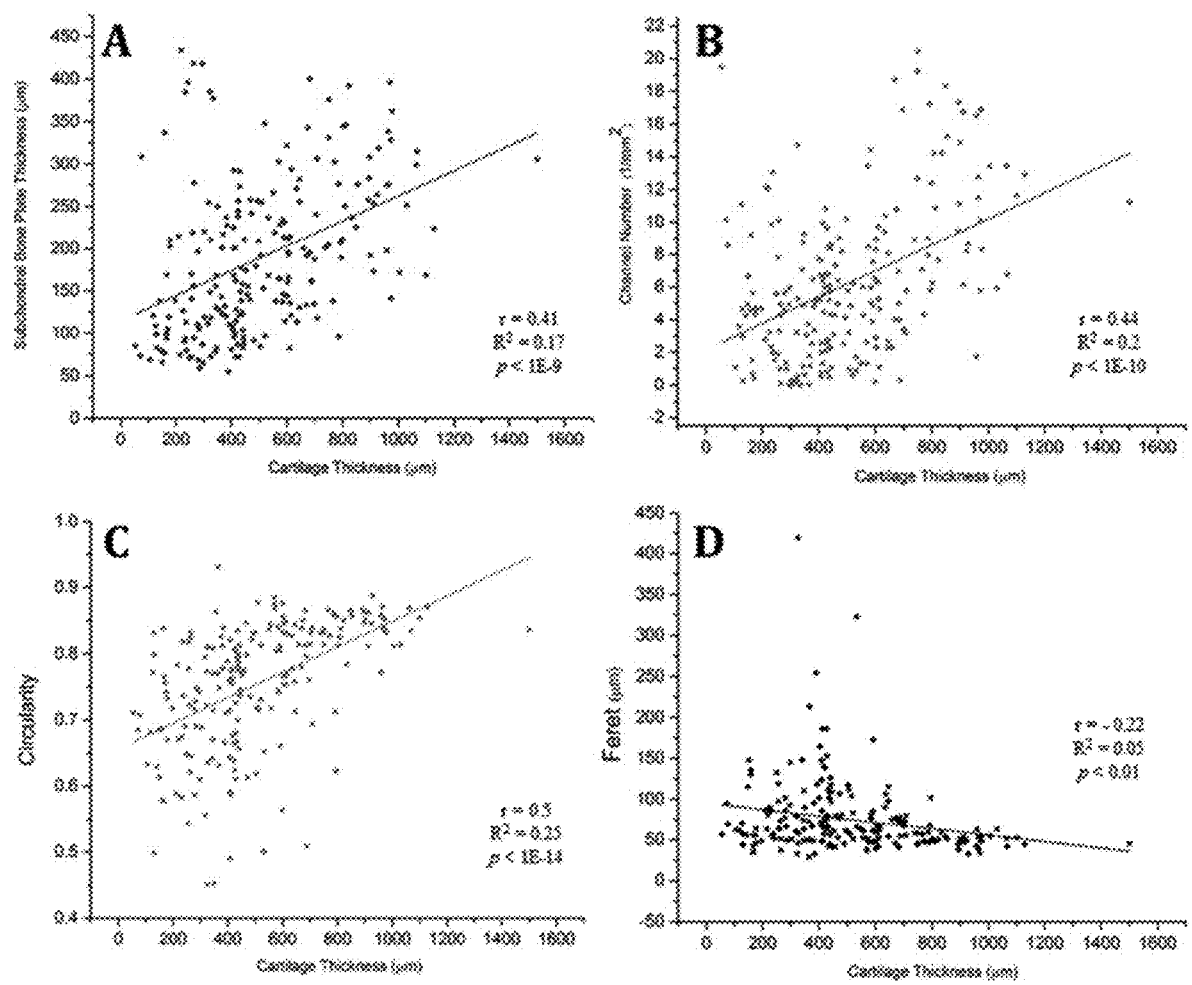

The present inventors observed several correlations between the SB microarchitecture and the overlying cartilage thickness. Subchondral bone plate (SBP) thickness, Ch.N., and Circ. were positively correlated with the cartilage thickness, having respective Pearson's r of 0.41, 0.44, and 0.5 (FIG. 2EA-EC). The size of the microchannels showed a slight negative correlation with cartilage thickness (r=−0.22; FIG. 2E at box D, bottom right-hand side).

Example 3

Pre-operative clinical examination was conducted on the subjects, including observations of the severity of pain, swelling, crepitus and range of motion (ROM); during subsequent follow-up sessions with the subjects, a clinical examination was conducted. Standing radiographs, CT scan or MRI were collected pre-operatively and at follow-ups in order to estimate axial deformities, the grade of chondral defect, and any degenerative change (according to Kellgren-Lawrence classification [8]). All patients complete questionnaires preoperatively and at each follow-up including Lysholm [9], Tegner [10] and International Knee Documentation Committee (IKDC) [11] scores.

The surgeries were performed by an experienced surgeon; the location and the size of the OA-stricken lesions are noted along with the associated pathologies. After identifying the full-thickness chondral or subchondral lesions, the unstable cartilage is removed using a shaver and a hand-held angled curette. Once the exposed subchondral bone plate is thoroughly debrided, multiple microchannels are created using a micro-drill or a laser ablation device. The microchannels are placed at an angle of 85 degrees to the joint surface with a density of 10 per $mm^2$ (shown in FIG. 3). Care is taken not to damage the subchondral plate in between the channels. Once the holes are completed, the irrigation fluid pump pressure is lowered to visualize the release of fat droplets and blood from the microchannel holes into the knee. All instruments are then removed, and the incision is surgically closed.

Example 4

For inserting a membrane or implant (whichever applies), the pre-operative clinical examination is consisted of similar procedures as described in Example 3. This includes severity of pain, swelling, crepitus and range of motion (ROM); during subsequent follow-ups, clinical examination is conducted. Standing radiographs, CT scan or MRI is collected pre-operatively and at follow-ups in order to estimate axial deformities, the grade of chondral defect, and any degenerative change (according to Kellgren-Lawrence [8]). All patients complete questionnaires preoperatively and at each follow-up including Lysholm [9], Tegner [10] and International Knee Documentation Committee (IKDC) [11] scores.

The surgeries were performed by an experienced surgeon; the location and the size of the OA-stricken lesions are noted along with the associated pathologies. After identifying the full-thickness chondral or subchondral lesions, the unstable cartilage is removed using a shaver and a hand-held angled curette. When present, the calcified layer of cartilage is taken out using a burr or an ablation laser down to the plane, where connection to the underlying vascular plexus becomes apparent. Once the so exposed subchondral bone is thoroughly debrided, the membrane or implant is placed on top of the subchondral bone, and fixed using sutures. The choice of the membrane or implant (whichever applies) (in terms of the density of the microchannels per $mm^2$, size, and angle in relation to the joint surface) depends on whether the load bearing region or the non-load bearing region of the joint is treated (shown in FIG. 4).

Patients follow a low-loading post-operative rehabilitation program as suggested by Steadman [12] and are immediately placed on a continuous passive motion machine (CPM) for 6-8 h daily. Crutch-assisted touchdown weight-bearing ambulation is allowed from 4 to 6 weeks according to the size and location of the lesion. Thereafter, weight-bearing loading is gradually increased, along with strength training, to achieve full weight bearing at 8 weeks. At further follow-ups, the condition of the membrane or implant, its integration, and its effect on the (sub)chondral bone and cartilage are monitored and examined.

Example 5

Generation of a Membrane for Implantation into a Knee Joint

Biocompatible polycaprolactone membrane(s) (thickness: 150 μm) is (are) provided with through holes by a micro-drill in order to mimic a preferred embodiment of the healthy subchondral bone. Thus, the through holes of the membrane(s) are arranged in size and distribution patterns that correspond to the microchannel patterns of the physiological load bearing region, non-load bearing region and peripheral rim of subchondral bone. Either a continuous membrane comprising different sections, i.e. a load bearing region section and/or a non-load bearing region section and/or a peripheral rim section, or separate membranes comprising only one specific section of the above may be provided.

Figure 5A:
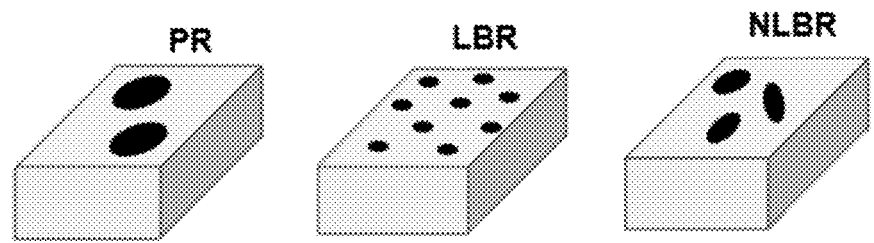
FIG. 5A: Membranes with different channel structures based on preferred embodiments corresponding to the respective SB areas are available.

After drilling, the membrane(s) comprise(s) 10 through holes per $mm^2$ of membrane in the load bearing region (LBR), each with a cross-sectional area of 1200 $\mu m^2$; 6 through holes per $mm^2$ of membrane in the peripheral rim (PR), each with a cross cross-sectional area of 3500 $\mu m^2$; and 4 through holes per $mm^2$ of membrane in the non-load bearing region (NLBR), each with a cross cross-sectional area of 1800 $\mu m^2$, respectively (shown in FIG. 5A). A continuous membrane or separate membranes comprising a plurality of through holes corresponding to preferred embodiments of load bearing region section, a non-load bearing region section and a peripheral rim section is (are) provided to the surgeon.

Figure 5B:
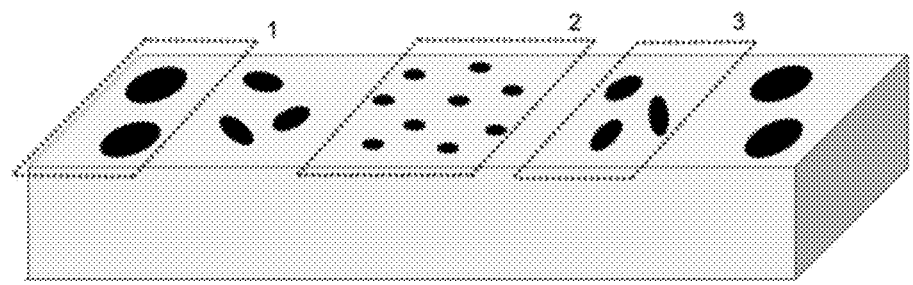
FIG. 5B: In healthy subchondral bone, channel configuration differs in the different areas of the joint, i.e. PR (1), LBR (2) and NLBR (3) (see also FIG. 1A to FIGS. 1D and 2).
Figure 5C:
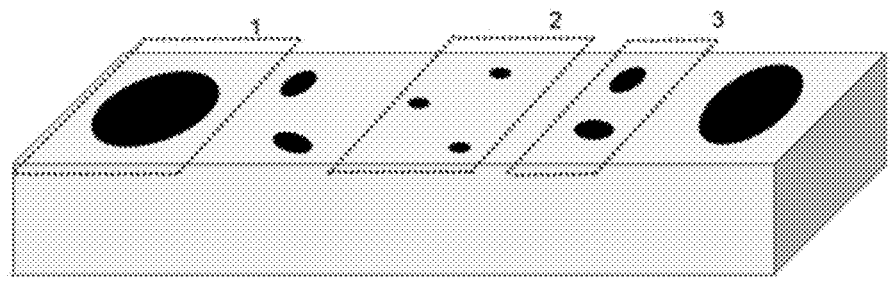
FIG. 5C: Pathological channel configurations differ from that present in healthy bone (as shown in FIG. 5B).
Figure 5D:
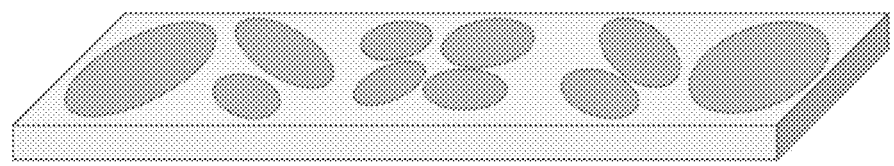
FIG. 5D shows a layer of pathological SB. Removal of pathological SB reveals underlying SB structures with increased number and cross-sectional area of microchannels.

The membrane(s) serve(s) for implantation in a knee joint. Prior to implantation, the channel size and number of the superior surface of the healthy subchondral bone (shown in FIG. 5B) differs from the pathologic subchondral bone of the patient (shown in FIG. 5C). The upper part of this pathological SB is then removed by microsurgery techniques. This leads to a layer of subchondral bone with increased number and cross-sectional area of microchannels at the most superior surface (shown in FIG. 5D). Typically, an increase of the microchannel cross-sectional area by a slope of 0.2-0.5 in the remaining SB as compared to the pathologic removed SB is expected. This procedure should provide a sufficient area of holes within the SB to allow sufficient access to the underlying bone marrow and vascular structures. Bleeding through the channels will indicate to the surgeon that the connection is achieved.

Figure 5E:
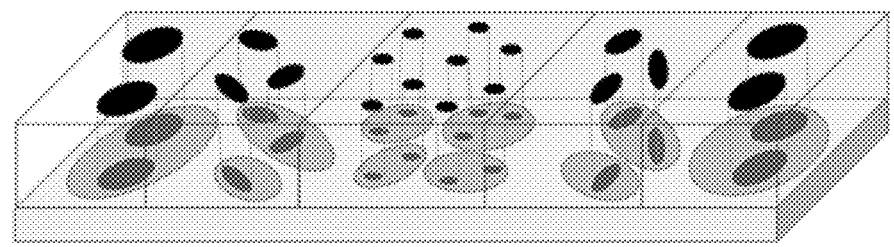
FIG. 5E: Corresponding membranes are fixed on the microsurgically pretreated SB to reinstate a physiologic size/number of channels (reflecting healthy SB microarchitecture).

Depending on preferred channel structure in the different loading areas of the joint, appropriate membranes are selected by the surgeon. The membranes are then surgically implanted on top of the microsurgically pretreated subchondral bone (shown in FIG. 5E). This ultimately re-introduces the physiological amount of continuous openings from the upper surface of the subchondral bone of the subject to the underlying trabecular bone spacing and its contents after the implantation. The membrane is fixed on the bone by fibrinogen glue and suturing as necessary.

REFERENCES

1. Yuan, X. L.; Meng, H. Y.; Wang, Y. C.; Peng, J.; Guo, Q. Y.; Wang, A. Y.; Lu, S. B. Bone-cartilage interface crosstalk in osteoarthritis: potential pathways and future therapeutic strategies. *Osteoarthr. Cartil.* 2014, 22, 1077-1089, doi:10.1016/j.joca.2014.05.023.
2. Goldring, S. R. Alterations in periarticular bone and cross talk between subchondral bone and articular cartilage in osteoarthritis. *Ther. Adv. Musculoskelet. Dis.* 2012, 4, 249-258, doi:10.1177/1759720X12437353.
3. Loeser, R. F.; Goldring, S. R.; Scanzello, C. R.; Goldring, M. B. Osteoarthritis: a disease of the joint as an organ. *Arthritis Rheum.* 2012, 64, 1697-707, doi:10.1002/art.34453.
4. Chen, D.; Shen, J.; Zhao, W.; Wang, T.; Han, L.; Hamilton, J. L.; Im, H.-J. Osteoarthritis: toward a comprehensive understanding of pathological mechanism. *Bone Res.* 2017, 5, 16044, doi:10.1038/boneres.2016.44.
5. Woods, C. G.; Greenwald, A. S.; Haynes, D. W. Subchondral vascularity in the human femoral head. *Ann. Rheum. Dis.* 1970, 29, 138-142, doi:10.1136/ard.29.2.138.
6. Lyons, T. J.; McClure, S. F.; Stoddart, R. W.; McClure, J. The normal human chondro-osseous junctional region: evidence for contact of uncalcified cartilage with subchondral bone and marrow spaces. *BMC Musculoskelet. Disord.* 2006, 7, 52, doi:10.1186/1471-2474-7-52.
7. Holzer, L. A. Die Bedeutung des subchondralen Knochens bei der Initiation und Progression der Arthrose. *Journal für Mineralstoffwechsel & Muskoskelettale Erkrankungen.* 2017, 24(1), 4-8.
8. Kellgren, J. H.; Lawrence, J. S. Raiological assessment of osteo-arthritis. *Ann. Rheum. Dis.* 1957, 16(4): 494-502.
9. Lysholm, J.; Gillquist, J. Evaluation of knee ligament surgery results with special emphasis on use of a scoring scale. *Am. J. Sports Med.* 1982, 10, 150-154, doi:10.1177/036354658201000306.
10. Tegner, Y.; Lysholm, J. Rating systems in the evaluation of knee ligament injuries. *Clin. Orthop. Relat. Res.* 1985, 43-9.
11. Irrgang, J. J.; Anderson, A. F.; Boland, A. L.; Harner, C. D.; Kurosaka, M.; Neyret, P.; Richmond, J. C.; Shelborne, K. D. Development and Validation of the International Knee Documentation Committee Subjective Knee Form. *Am. J. Sports Med.* 2001, 29, 600-613, doi:10.1177/03635465010290051301.
12. Steadman, J. R.; Rodkey, W. G.; Rodrigo J. J. Microfracture: Surgical Technique and Rehabilitation to treat chondral defects. *Clin. Orthop. Relat. Res.* 2001, (391 Suppl.): S362-9.

What is claimed is:

1. A biocompatible membrane or implant comprising a plurality of through holes, wherein the biocompatible membrane or implant comprises between 5 and 20 through holes per $mm^2$ of the membrane or implant, wherein the through holes are arranged in a size and distribution pattern that correspond to a pattern of microchannels of one or more of load bearing regions, non-load bearing regions or a peripheral rim of subchondral bone of a joint of a subject, wherein the through holes provide for a continuous opening within the biocompatible membrane or implant configured to connect a base bone facing surface of the subchondral bone with an upper synovium facing surface, wherein the biocompatible membrane or implant is distributed among one or more of a load bearing region section, a non-load bearing region section and/or a peripheral rim section; wherein each of the plurality of through holes in the load bearing region section defines a cross-sectional area of between 800 $\mu m^2$ and 1600 $\mu m^2$, each of the plurality of through holes in the non-load bearing region section defines a cross-sectional area of between 1600 $\mu m^2$ and 2500 $\mu m^2$, and each of the plurality of through holes in the peripheral rim section defines a cross-sectional area of between 2500 µm² and 4000 µm²; and wherein the membrane or implant has a thickness of between 50 µm and 150 µm.

2. The biocompatible membrane or implant of claim 1, wherein the membrane or implant further comprises cells adhered thereto.

3. The biocompatible membrane or implant of claim 1, wherein the membrane or implant is biodegradable.

4. The biocompatible membrane or implant of claim 1, wherein the permeability of the membrane or implant corresponds to the permeability of a healthy joint in a subject based on corresponding reference data obtained from the same joint at an earlier time point.

5. The biocompatible membrane or implant of claim 1, wherein the implant is a hip, knee, elbow, or shoulder implant.

6. A method of treating a joint of a subject in need thereof, wherein the method comprises: a) introducing through holes into a subchondral bone region in the joint; and b) applying a biocompatible membrane or implant to the subchondral bone region, wherein the biocompatible membrane or implant comprises between 5 and 20 through holes per mm² of the membrane or implant, wherein the through holes are arranged in a size and distribution pattern that correspond to a pattern of microchannels of one or more of load bearing regions, non-load bearing regions or a peripheral rim of subchondral bone of a joint of a subject, wherein the through holes provide for a continuous opening within the biocompatible membrane or implant configured to connect a base bone facing surface of the subchondral bone with an upper synovium facing surface, wherein the membrane or implant has a thickness of between 50 µm and 150 µm; wherein the through holes introduced in step a) are arranged in a size and distribution pattern that correspond to the pattern of microchannels of one or more of the load bearing region, non-load bearing region or peripheral rim of the healthy subchondral bone; and wherein each of the plurality of through holes in the load bearing region defines a cross-sectional area of between 800 µm² and 1600 µm², each of the plurality of through holes in the non-load bearing region defines a cross-sectional area of between 1600 µm² and 2500 µm², and each of the plurality of through holes in the peripheral rim defines a cross-sectional area of between 2500 µm² and 4000 µm².

7. The method of claim 6, wherein the joint is a human knee joint.

8. The method of claim 6, wherein the through holes introduced in step a) are arranged in a pattern of between 5 and 20 through holes per mm² on the subchondral bone, and comprise a length corresponding to the thickness of the subchondral bone of the subject.

9. The method of claim 6, wherein the through holes introduced in step a) are arranged in a pattern of between 5 and 10 through holes per mm² on the subchondral bone, and comprise a length corresponding to the thickness of the subchondral bone of the subject.

10. The method of claim 6, wherein the through holes introduced in step a) are arranged in a pattern of 10 through holes per mm² on the subchondral bone and comprise a length corresponding to the thickness of the subchondral bone of the subject.

11. The method of claim 6, wherein the method further comprises:
removing diseased subchondral bone tissue from the joint of the subject, prior to performing step a).

* * * * *